United States Patent
Dunbar

(10) Patent No.: US 11,766,502 B2
(45) Date of Patent: Sep. 26, 2023

(54) METHOD, APPARATUS AND SYSTEM FOR REDUCING PATHOGENS IN A BREATHABLE AIRSTREAM

(71) Applicant: TOMPHYZX.LLC, Dundee, NY (US)

(72) Inventor: Thomas Dunbar, Dundee, NY (US)

(73) Assignee: TOMPHYZX.LLC, Dundee, NY (US)

( * ) Notice: Subject to any disclaimer, the term of this patent is extended or adjusted under 35 U.S.C. 154(b) by 0 days.

(21) Appl. No.: 17/402,025

(22) Filed: Aug. 13, 2021

(65) Prior Publication Data

US 2022/0047898 A1  Feb. 17, 2022

Related U.S. Application Data

(60) Provisional application No. 63/221,895, filed on Jul. 14, 2021, provisional application No. 63/150,126, filed on Feb. 17, 2021, provisional application No. 63/113,304, filed on Nov. 13, 2020, provisional application No. 63/065,205, filed on Aug. 13, 2020.

(51) Int. Cl.
| | | |
|---|---|---|
| *A61L 9/20* | (2006.01) | |
| *A62B 18/02* | (2006.01) | |
| *A62B 18/10* | (2006.01) | |

(52) U.S. Cl.
CPC .............. *A61L 9/20* (2013.01); *A62B 18/025* (2013.01); *A62B 18/10* (2013.01); *A61L 2209/111* (2013.01); *A61L 2209/12* (2013.01); *A61L 2209/14* (2013.01); *A61L 2209/16* (2013.01)

(58) Field of Classification Search
None
See application file for complete search history.

(56) References Cited

U.S. PATENT DOCUMENTS

| | | | |
|---|---|---|---|
| 8,205,622 | B2 | 6/2012 | Pan |
| 9,480,768 | B2 | 11/2016 | Krosney et al. |
| 10,130,726 | B2 | 11/2018 | Pujol et al. |
| 10,335,618 | B2 | 7/2019 | Zhou |
| 10,473,351 | B2 | 11/2019 | Anderson et al. |

(Continued)

FOREIGN PATENT DOCUMENTS

| | | |
|---|---|---|
| EP | 0461310 A1 | 12/1991 |
| EP | 1541179 A1 | 6/2005 |

(Continued)

OTHER PUBLICATIONS

Nagaki et al. (2020) "Rapid inactivation of SARS-CoV-2 with deep-UV LED irradiation," Emerging Microbes & Infections 9(1): 1744-1747.

(Continued)

*Primary Examiner* — Andrew Smyth
(74) *Attorney, Agent, or Firm* — Jodi A. Reynolds, Esq.; Harter Secrest & Emery LLP

(57) ABSTRACT

A handheld device for treating air to a user includes an airflow path having an illumination chamber with a reflective surface, wherein the reflective surface is sufficiently reflective and configured to impart multiple reflections of at least a portion of the light introduced into the illumination chamber. The introduced light is produced by an onboard UV light generator, wherein the UV light generator can be cycled corresponding to at least one of a pressure and an airflow in the airflow path.

26 Claims, 13 Drawing Sheets

(56) References Cited

U.S. PATENT DOCUMENTS

| | | | |
|---|---|---|---|
| 2007/0101867 A1* | 5/2007 | Hunter | A62B 23/02 96/224 |
| 2007/0207066 A1 | 9/2007 | Thur et al. | |
| 2008/0019861 A1 | 1/2008 | Silderhuis | |
| 2008/0152548 A1 | 6/2008 | Clark et al. | |
| 2009/0004047 A1* | 1/2009 | Hunter | A61L 9/205 422/4 |
| 2012/0168641 A1 | 7/2012 | Lizotte | |
| 2014/0158917 A1 | 6/2014 | Stibich et al. | |
| 2016/0296649 A1 | 10/2016 | Ramanand et al. | |
| 2018/0021471 A1 | 1/2018 | Krosney | |

FOREIGN PATENT DOCUMENTS

| | | | | |
|---|---|---|---|---|
| EP | 1918208 A1 | | 5/2008 | |
| FR | 2712815 A1 | * | 6/1995 | ........ A61M 16/0493 |
| WO | 2020013907 A1 | | 1/2020 | |
| WO | 2020163733 A1 | | 8/2020 | |
| WO | WO-2020257928 A1 | * | 12/2020 | .......... B01J 19/0053 |
| WO | 2021156876 A1 | | 8/2021 | |

OTHER PUBLICATIONS

International Search Report and Written Opinion of the International Searching Authority in corresponding International Application No. PCT/US2021/045922; dated Nov. 23, 2021.

International Search Report and Written Opinion of the International Searching Authority in corresponding International Application No. PCT/US2021/045948; dated Dec. 28, 2021.

Kowalski et al. (2000) "Mathematical Modeling of Ultraviolet Germicidal Irradiation for Air Disinfection," Quantitative Microbiology 2: 249-270.

Sagripanti et al. (2020) "Estimated Inactivation of Coronaviruses by Solar Radiation With Special Reference to COVID-19," Photochemistry and photobiology 96(4): 731-737.

UVMask: All-Day Active UV-C Air Purification Face Mask KickStarter Campaign (2020), retreived from https://www.kickstarter.com/projects/umsystems/uvmask-inactivate-9999-of-all-pathogens-and-air-pollutants? utm_source=kickbooster-direct&utm_medium=kickbooster&utm_content=link&utm_campaign=032652fa.

Walker et al. (2007) "Effect of Ultraviolet Germicidal Irradiation on Viral Aerosols," Environ. Sci. Technol. 41(15): 5460-5465.

* cited by examiner

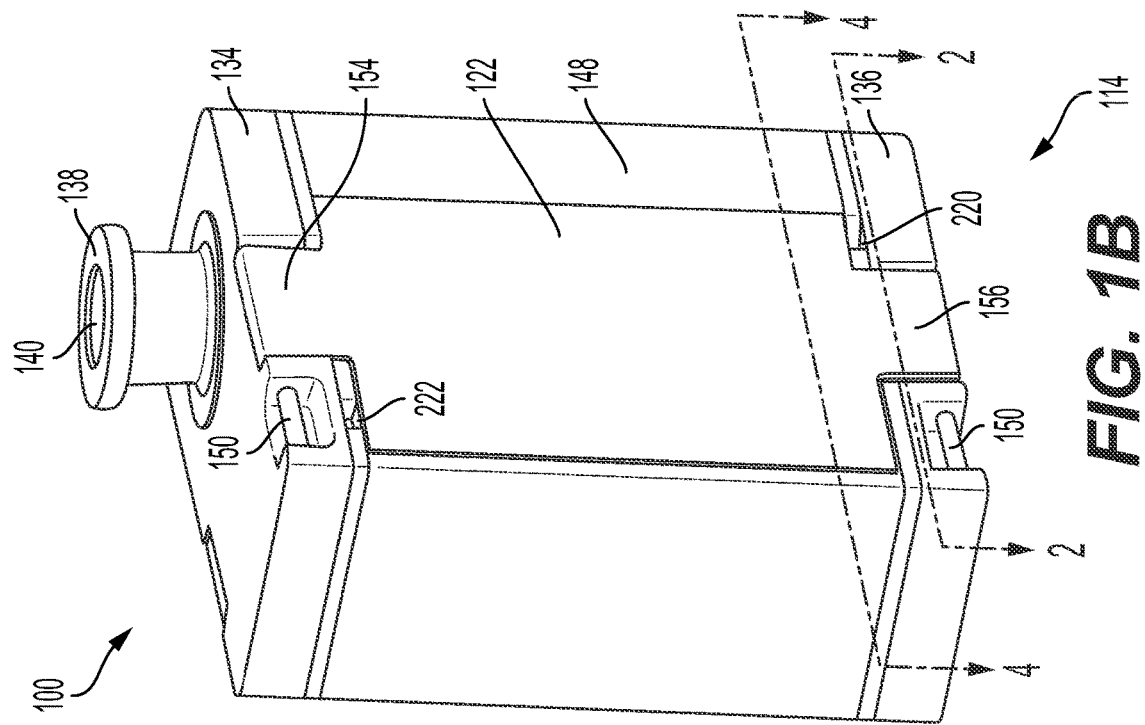
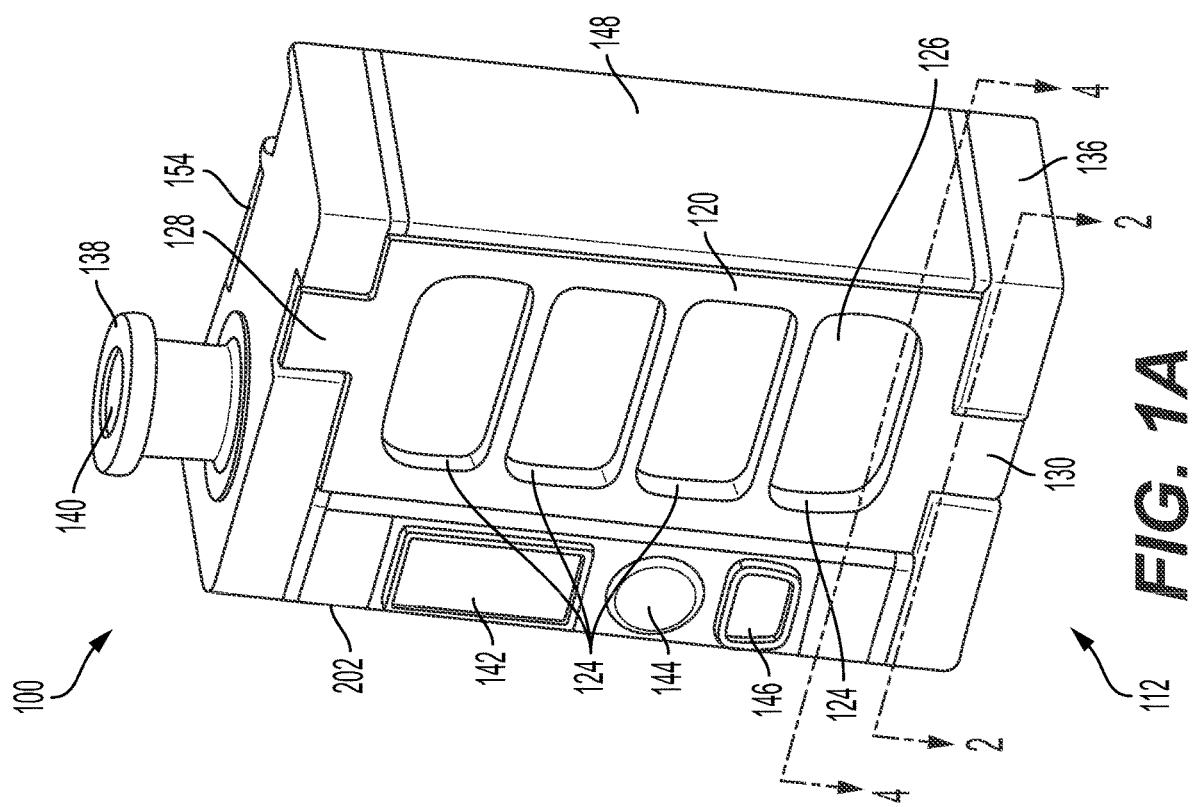

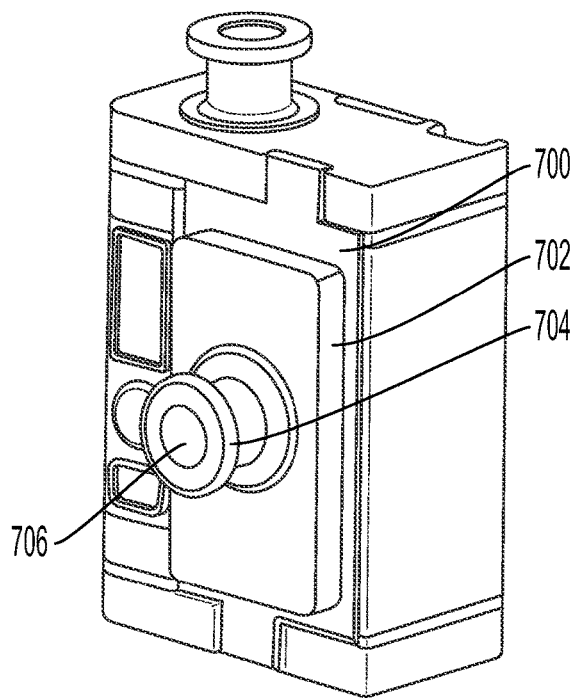 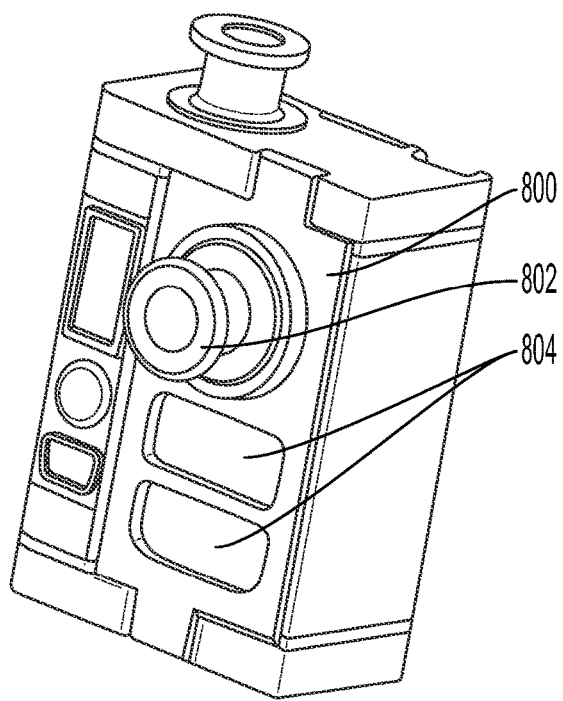
*FIG. 16*  *FIG. 17*

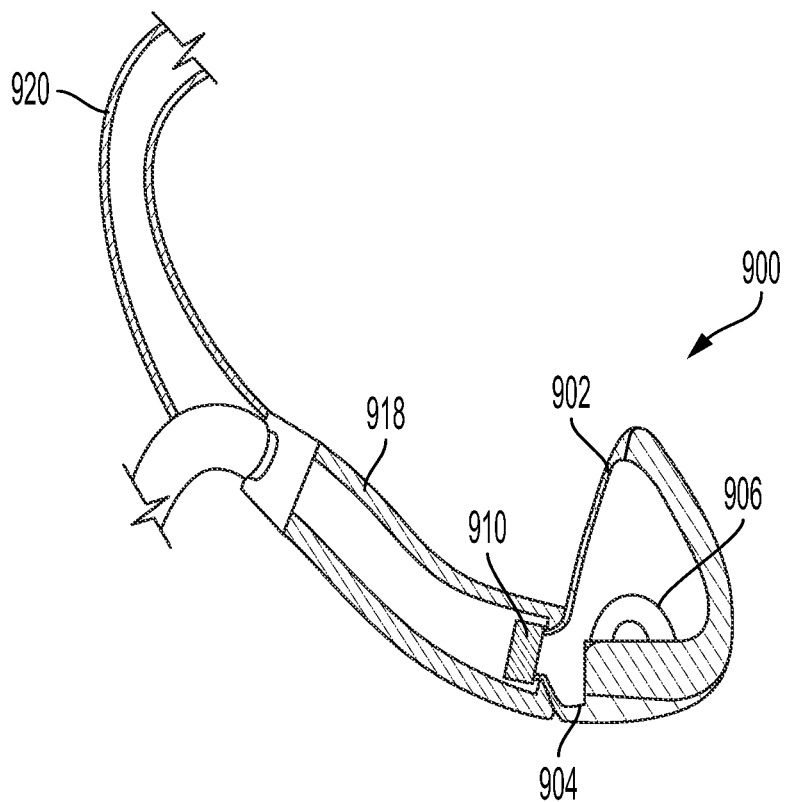
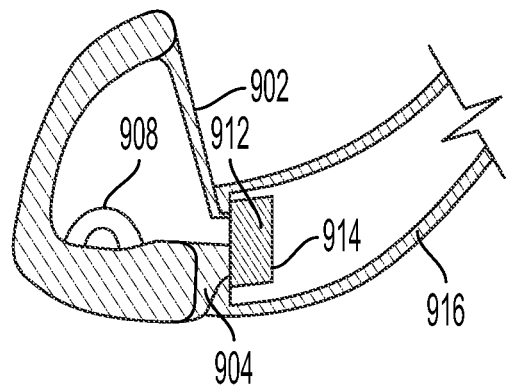
FIG. 23

METHOD, APPARATUS AND SYSTEM FOR REDUCING PATHOGENS IN A BREATHABLE AIRSTREAM

BACKGROUND OF THE INVENTION

Field of the Invention

The present invention relates to pathogen reduction systems, and more particularly, to methods, apparatuses and systems of reducing pathogens in an airstream through the pathogen reduction system.

Description of Related Art

The COVID-19 pandemic is changing the mindset of individuals as the public becomes more aware of the ability to prevent the transmission of communicable diseases. While it was once common to share an untreated airstream with others in an environment, whether enclosed or outside, many individuals are no longer comfortable in such settings. It has been found that wearing masks such as cloth masks, surgical masks, and particle-filtering face masks can greatly reduce the risk of transmitting and contracting COVID-19 and other airborne illnesses. These masks generally work by filtering particles in an airstream, for example respiratory droplets on a large scale, or aerosolized droplets and pathogens on a smaller scale.

However, many people find masks to be uncomfortable. This is because as a person breathes in, the mask filters the airstream and, in the process, slows the airflow being drawn into the nose or mouth of the person. The slower airflow can make breathing feel more difficult and restricted, especially if a wearer is breathing quickly or deeply, such as during exercise. Additionally, the flexible material of the mask can be sucked against the mouth and nose of a wearer during inhale, which generates even more discomfort and restriction to airflow.

Additionally, the filtering mechanism of masks can be inefficient in reducing pathogens from a breathed airstream. Many cloth masks are made from fabric which is permeable by pathogens that are small enough to fit between the weave of the fabric. Even masks that are made from material which is able to filter out particles on the scale of a virus particle can be inefficient if there is not an airtight seal between the mask and the wearer's face, since some air will bypass the filtering fabric altogether.

Further, most masks are designed to cover both the nose and mouth of a wearer. This makes wearing masks in certain settings is not practical. For example, in a restaurant, individuals cannot eat and wear a mask simultaneously. However, masks do provide some limited protection from airborne or aerosolized pathogens in an easily portable and relatively small-sized personal item that can fit in, for example, a backpack or a purse. Thus, it is desired to provide a system that can reduce the risk of COVID-19 exposure with increased efficiency, increased user comfort, and maximized pathogen reduction in the breathed airstream, while maintaining the portability and size convenience of a mask.

One option is to treat the air in the breathed airstream to reduce the pathogens in the airstream. Exposure of the airstream to a UV-C source, as measured in watts of UV-C energy, can provide a pathogen reduction system. A problem with existing pathogen reduction systems, however, is that they have limited sized illumination cavities and improper pathogen exposure to the UV energy to provide enough treated air in an environment to significantly reduce the pathogens in the environment. Another problem with existing pathogen reduction systems is that they are inefficient and ineffective at killing pathogens.

Further, the amount of UV-C illumination that makes it into the air flow in existing systems is too low. Existing systems specifications describe an illumination value that is defined in terms of watts per $cm^2$ (that is, power per unit area rather than power per unit volume) and not emitted power that passes through the air channel. Thus, the existing systems' UV-C power is not sufficient for adequate pathogen reduction applications. Since Exposure as measured in joules of UV-C energy per exposure chamber volume and is the primary purpose of UV-C based pathogen reduction systems, the present system improves upon existing systems by implementing significantly higher exposures utilizing a linear length of high UV-C reflectance surfaces, such as but not limited to mirrored anodized aluminum or PTFE (polytetrafluoroethylene) materials.

Finally, existing pathogen reduction systems utilize fans, blowers, pumps, or other mechanical means to generate an air flow. These machine means of moving an airstream often use power from a power source. This limits the ultimate efficiency of any pathogen reduction system that uses a finite or limited rechargeable power source in that less power is available for generating light or pathogen reduction since it is used by the fan, blower, or pump. The fan, blower, or pump also provides an additional machine component that might break or otherwise mechanically fail, rendering the system useless. Thus, a pathogen reduction system is desired that can maximize power conservation and efficiency while also maximizing the effective pathogen reduction per watt of energy used.

BRIEF SUMMARY OF THE INVENTION

Embodiments of the present disclosure provide an airflow system for reducing pathogens in a breathable airstream environment.

In one configuration, the present disclosure provides an apparatus for presenting treated air to a user, wherein the apparatus includes a handheld housing, a power source retained in the handheld housing, a controller in the handheld housing and operably connected to the power source, a flow path extending through the handheld housing from an inlet to an outlet, a UV generator in the handheld housing, the UV generator optically coupled to the flow path, and a mouthpiece at the outlet, the mouth piece configured to sealingly engage a mouth of the user.

In a further configuration, the present disclosure provides an apparatus for presenting treated air to a user, wherein the apparatus includes a body having at least one inlet and at least one outlet, a power source, a flow path through the body from the at least one inlet to the at least one outlet, and an illumination chamber in the flow path, the illumination chamber including a UV light source in electrical connection with the power source and operable to emit photons over time and UV reflective walls, wherein at least a portion of the photons emitted by the UV light source are reflected by the UV reflective walls at least five times.

The present disclosure also includes a method of presenting treated air to a user, wherein the method includes the steps of sealingly engaging a mouth with a mouthpiece of the handheld housing; and drawing air through a flow channel in the handheld housing to impart an initiation signal to a controller retained in a handheld housing and to expose the drawn air to UV radiation.

A method is further provided of presenting treated air to a user, wherein the method includes cycling a UV light source to emit photons into an air flow in an illumination chamber in an airflow channel, wherein at least a portion of the emitted photons are reflected within the illumination chamber at least 3 times; and cycling the UV light source to terminate emitting photons corresponding to at least one of a flow through the airflow channel and a pressure in the airflow channel.

BRIEF DESCRIPTION OF THE SEVERAL VIEWS OF THE DRAWING(S)

FIG. 1A is a front perspective view of an airflow pathogen reduction system suitable for use in practicing exemplary embodiments of this disclosure;

FIG. 1B is a rear perspective view of the airflow pathogen reduction system shown in FIG. 1A;

FIG. 16 is a perspective view of the airflow pathogen reduction system with a variation of the front door;

FIG. 17 is a perspective view of the airflow pathogen reduction system with a variation of the front door;

FIG. 23 is a perspective view of an exemplary embodiment of the user-end connector of the airflow pathogen reduction system;

DETAILED DESCRIPTION OF THE INVENTION

Figure 1C:
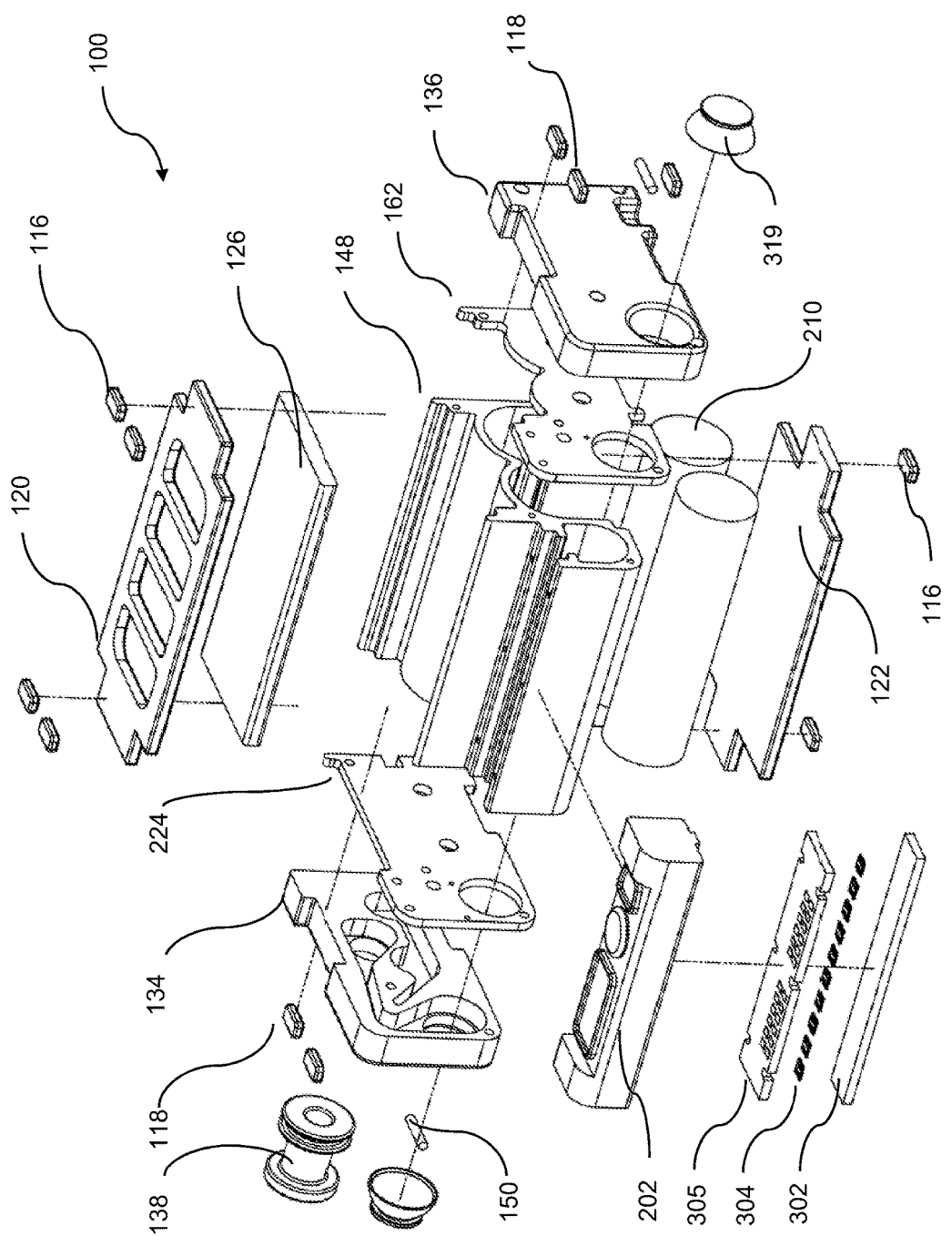
FIG. 1C is an exploded view of the airflow pathogen reduction system shown in FIGS. 1A and 1B.

Referring to FIGS. 1A-C, an airflow pathogen reduction device 100 is shown. In one configuration, the device 100 is a hand-held device.

The form factor of the hand-held device is generally a device that can easily be held in one hand. It is understood the hand-held device may be directed at one-handed operation or two-handed operation. In one-handed operation, a single hand is used to both support the device as well as to perform operations during use. In two-handed operation, one hand is used to support the device while the other hand performs operations with the device. It is recognized that hand-held devices may have a variety different footprints or sizes such as a device that can be typically placed in a pocket while larger devices are separately carried. Generally it is preferred, although not necessary, that hand-held devices of the type disclosed herein have dimensions with a height between 3 and 5 inches, a width between 2 and 4 inches, and a depth between 0.5 and 2 inches.

The term airflow pathogen reduction device 100 can encompass any system or device capable of inactivating pathogens in an airflow and embodiments of the present disclosure are not limited to the particular configuration of airflow pathogen reduction device 100. By pathogen, it is meant any virus, bacterium, or other disease-causing microorganism.

The airflow pathogen reduction device 100 generally includes a body 148, a bottom cap 136, a top cap 134, an embedded mouthpiece 138, an electronics module 202, a front door 120 and a rear door 122. The doors 120,122 are generally rectangular, with two tabs on each door that extend out from the rectangle shape in the same plane as the door 120,122. The front door 120 includes a front door top tab 128 and a front door bottom tab 130. Similarly, the rear door 122 includes a rear door top tab 154 and a rear door bottom tab 156. Each of the four tabs 128,130,154,156 contains an embedded magnet 116 configured to releasably magnetically couple the door 120,122 to the magnets embedded in the top cap 136 and bottom cap 134 in corresponding locations to the magnets embedded in the doors 120 and 122 top and bottom tabs. It should be understood that the doors 120,122 can alternatively or additionally be coupled to the device with other fasteners known in the art. Front door 120 also has intake apertures 124 that allow airflow to pass through the front door 120, from the ambient environment into the airflow pathogen reduction device 100. The apertures can vary in size and shape to allow different patterns and volumes of airflow to pass into the system. In an embodiment, a filter media 126 sits behind front door 120 and is visible through intake apertures 124. Filter media 126 can be any suitable filtration media known in the art for filtering an airflow. This includes, but is not limited to, fiberglass, plastics, activated carbon, or plant-based filtration materials.

Figure 4:
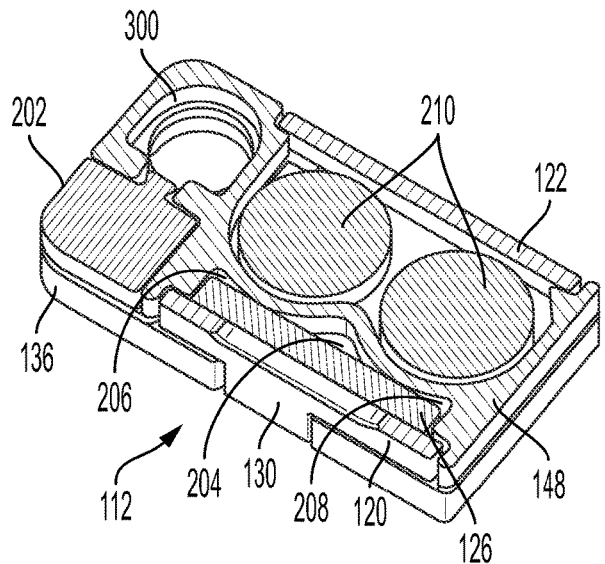
FIG. 4 is the perspective view of the cross section of the airflow pathogen reduction system taken along lines 4-4 of FIGS. 1A and 1B, and including a body atop the bottom plate.
Figure 24A:
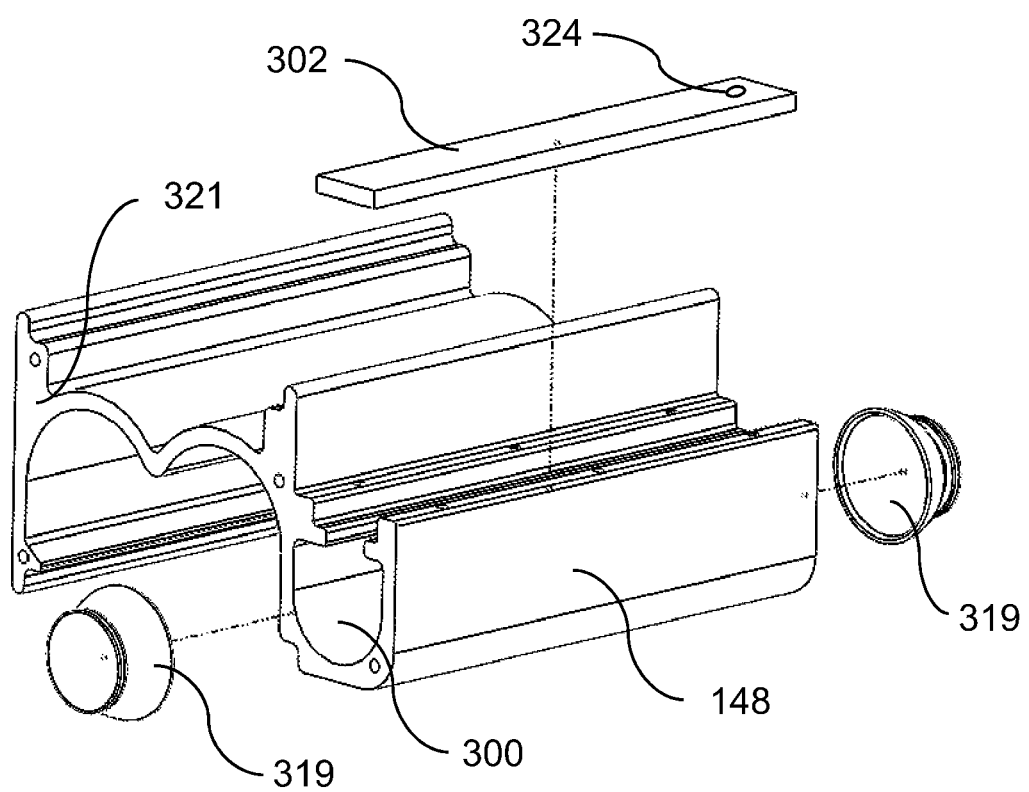
FIG. 24A is a perspective exploded view of an exemplary embodiment of the body and the illumination chamber; and, FIG. 24B is a cross-sectional view of the illumination chamber.

The doors 120,122 are configured to fit within spaces framed partially by body 148 and partially framed by the top and bottom caps 134,136. Body 148 is a single piece which composes some of the external walls of airflow pathogen device 100, and also defines some internal spaces in airflow pathogen device 100 with its shape, when airflow pathogen device 100 is assembled. FIG. 4 shows a cross-sectional view of the shape of body form 148. FIG. 24A shows a perspective view of body 148 and top edge 321. Body 148 is substantially symmetrical such that any other cross-section of body 148 should be substantially the same shape as what is pictured in FIG. 4. In an embodiment, body 148 is made from anodized aluminum material. In another embodiment, body 148 is made of a PTFE material such as POREX® Virtek™ PTFE made by Porex Filtration Group. In another embodiment, body 148 is made from another suitable material known in the art, such as metal, polymer, plastics, or another suitable material, and a UV-C reflective surface coating or lining on the portion of body 148 defining an illumination chamber 300.

Figure 24B:
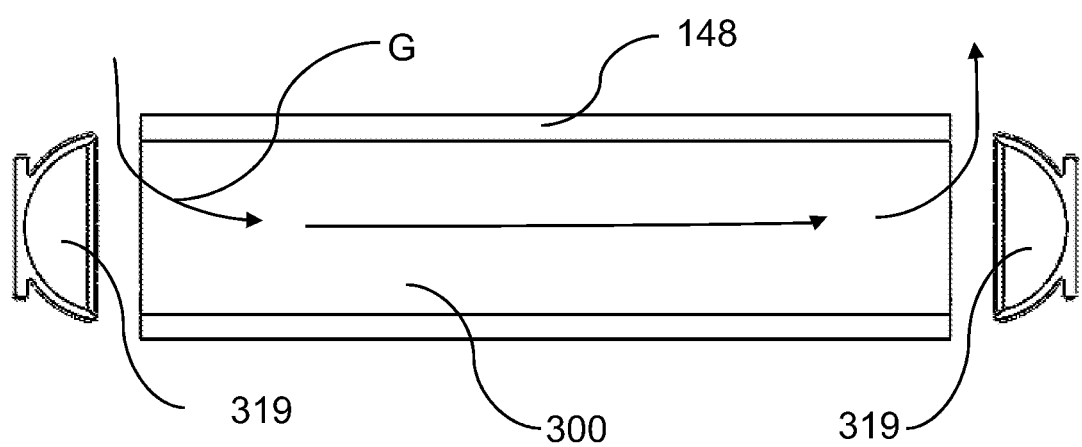

At each end of the illumination chamber 300 is a UV-C reflective cap 319. The reflective caps 319 are imbedded in the top cap 134 and the bottom cap 136, respectively. In one embodiment, the caps 319 are semi-spherical, and are oriented in the top and bottom caps 134,136 such that the apexes of the semi-spheres are arranged distal to the body 148 and the illumination chamber 300, and the rims of the semi-spheres are arranged proximal to the body 148 and the illumination chamber 300, which orientation is shown in FIGS. 24A-B. The shape of these caps is optimized to reflect UV-C light escaping the illumination cavity back into the cavity. The shape of these caps is one of semi-spherical, parabolic, flat, aspheric, conical or other shapes know in the art. FIG. 24B shows a section view of the components of the illumination chamber normal to the long axis of the device 100. The flow path G, enters through the gap shown in the left side of the view through the illumination chamber and out a corresponding gap in the right side of the view. These gaps are maintained in the structure by imbedding each reflective cap 319 into each cap 134,136 such that the rim of cap 319 sits below the planar surface of cap 134,136. This leaves a gap between the end of the illumination chamber and the edge of reflective cap 319, and thereby allows airflow to pass through the gap into and out of the illumination chamber 300.

The bottom edge of body 148 is attached to the bottom plate 162, which itself is attached to bottom cap 136. Bottom cap 136 can include two embedded magnets 118, which are configured to magnetically couple with the two embedded magnets 116 in the intake front door bottom tab 130 and battery cover rear door bottom tab 156. The top edge of body 148 is attached to top plate 224, which is attached to top cap 134. Top cap 134 can also include two embedded magnets 118, which are configured to magnetically couple with the two embedded magnets 116 in intake front door top tab 130 and battery cover rear door top tab 154. Magnetically attached in this way, the doors 120,122 are releasably attached to top cap 134 and bottom cap 136 and are maintained in position against body 148, which is maintained between top cap 134 and bottom cap 136. It should be understood that any number of magnets 116 and complimentary magnets 118 can be used in the present disclosure to releasably attach doors 120,122 to top and bottom caps 134,136. Body 148 has a shape that specifically generates bezel spaces for doors 120,122 to fit into. Rear door 122, when attached to the fully assembled device 100, is framed on its top edge by top cap 134, on its bottom edge by bottom cap 136, and on both sides by edges of body 148. Front door 120, when attached to the fully assembled device 100, is framed on its top edge by top cap 134, on its bottom edge by bottom cap 136, and on both sides by an edge of body 148.

Body 148 also defines a space for electronics module 202. The top edge of electronics module 202 is attached to top plate 224, which is attached to top cap 134, and the bottom edge of electronics module 202 is attached to bottom plate 162, which is attached to bottom cap 136. Electronics module 202 is a generally elongated cuboid shape, with a protruding ridge traveling the length of the electronics module 202 in the center of one long facet of the cuboid. The protruding ridge houses the UV-C light generator 304, the thermal management component 305, and optical window 302. Electronics module 202 includes four long facets and two ends, wherein each long facet is joined to the two adjacent long facets by a corner length. When airflow pathogen reduction device 100 is fully assembled, two facets of electronics module 202 and the facets' single shared corner are fully enclosed within the interior of device 100. The corner opposite the fully enclosed corner is rounded in shape and is external to device 100, such that it defines a rounded outer corner of device 100. Electronics module 202 contains at least a controller. The controller includes electrical circuits, such as signal processors, and can be implemented as a programmed chip, as well as a dedicated processor or circuitry. The controller can be readily programmed to perform the recited calculations, or derivations thereof, to provide determinations of the detector as set forth herein.

One of the long facets of electronics module 202 is on the front 112 of device 100. This front facing facet includes display 142, control button 144, and charge port 146. Display 142 is attached to the controller contained within electronics module 202. Display 142 is configured to display information to a user. This can include battery status, filter life, light source life, date and time, and various other information that could be useful to a user. Control button 144 can communicate to the controller and control functions of the device or of the display 142. Charging port 146 provides a port for recharging batteries 210 using any of the power charging mating connectors known in the art.

Top cap 134 and bottom cap 136 each include a strap holder 150. Strap holder 150 enables a user to attach a strap to airflow pathogen reduction device 100, which can make it easier for a user to hold, store, or use device 100. Additionally, in the rear 114 of device 100 there are battery vents 220, 222 which allow heat and air to vent from battery chamber 246 to the ambient air surrounding device 100.

Figure 2:
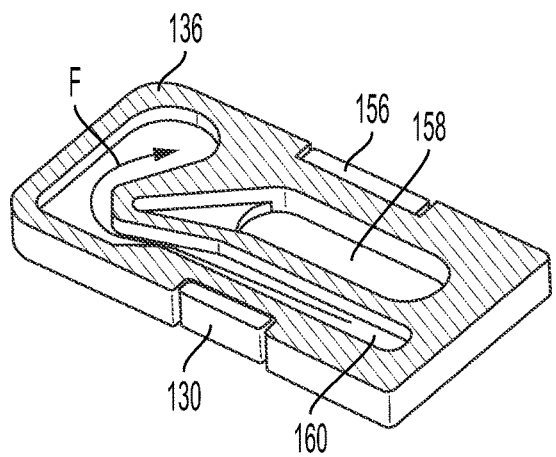
FIG. 2 is a perspective view of a cross section of the airflow pathogen reduction system taken along lines 2-2 of FIGS. 1A and 1B showing a bottom cap.

FIG. 2 shows a cross-section of the airflow pathogen reduction device of FIGS. 1A-C. This cross-sectional view shows the bottom cap 136, which contains bottom battery connection cavity 158 and bottom cap air channel 160. Bottom battery connection cavity 158 is a recess that is configured to receive battery connections and electrical wiring. Bottom cap air channel 160 is a recessed cavity to receive airflow and guide the airflow to entrance hole 168 to illumination chamber 300. Bottom cap air channel 160 generally includes an elongate section and a wider section. An airflow originating from outside the system, for example from the ambient environment, is received to the elongate section of air channel 160. The airflow then follows path F from the elongate section to the wider section. From the wider section of air channel 160 the airflow will travel upwards into illumination chamber 300.

Figure 3:
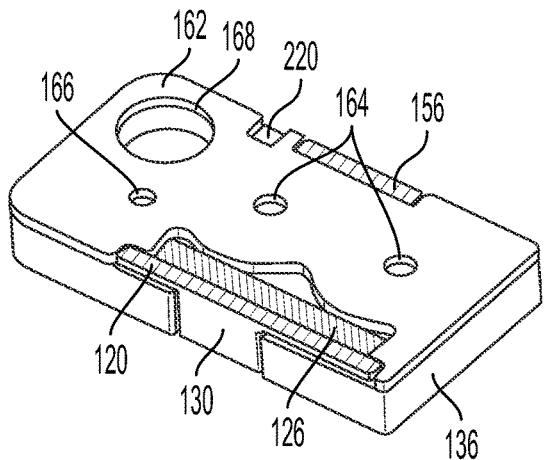
FIG. 3 is the perspective view of the cross section of the airflow pathogen reduction system shown in FIG. 2 and including a bottom plate assembled atop the bottom cap.

FIG. 3 shows the cross-section of the airflow pathogen reducing device of FIG. 2. This cross-sectional view shows bottom cap 136 with bottom plate 162 assembled atop bottom cap 136. Bottom plate 162 is generally planar, with various apertures through the plate 162. Bottom wire hole 166 carries a battery wire from bottom battery connection cavity 158 through the bottom wire hole 166. Entrance hole 168 allows movement of air from bottom cap air channel 160 up through bottom plate 162 and into illumination chamber 300. Bottom battery holes 164 provide a retaining means for a battery spring button connector, and allow for wires to travel from the battery chamber 246 to bottom battery connection cavity 158. Additionally, bottom vent hole 220 is an aperture at the edge of bottom plate 162 that allows heat and air to flow out of battery chamber 246. Filter media 126 is held behind front door 126, and behind filter media 126 is a set of three vertical air channels 204,206,208. The central vertical air channel 204 is larger than the two peripheral vertical air channels 206,208. The vertical air channels are defined by body frame 148 and the filter media 126. It should be understood that any number of vertical air channels, including one single channel, is also suitable to be used in this device 100.

Figure 5:
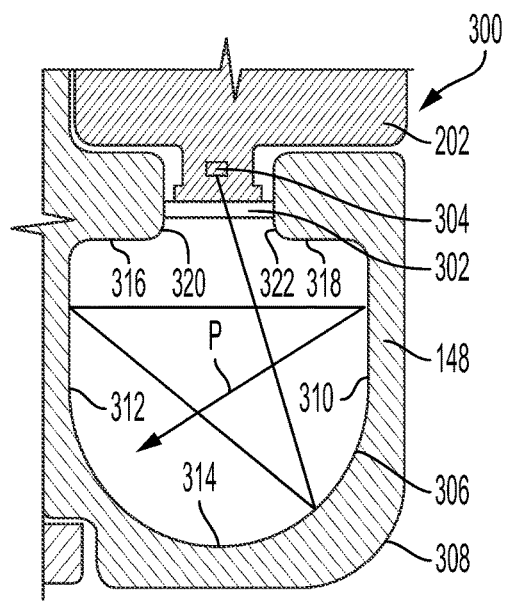
FIG. 5 is a partial cross-sectional view of the illumination chamber of the airflow pathogen reduction system shown in FIG. 4, suitable for use in practicing exemplary embodiments of this disclosure.
Figure 6A:
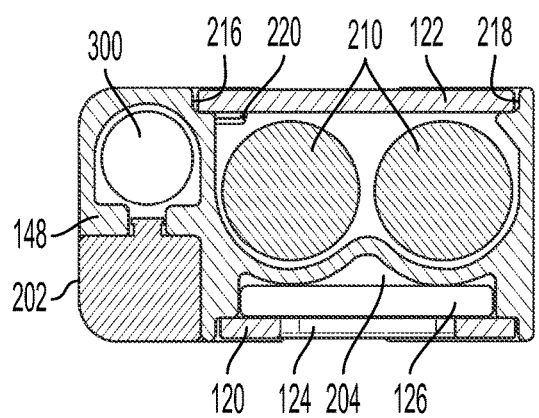
FIG. 6A is a top view of the cross-sectional view of the airflow pathogen reduction system shown in FIG. 4, looking towards the bottom cap.
Figure 6B:
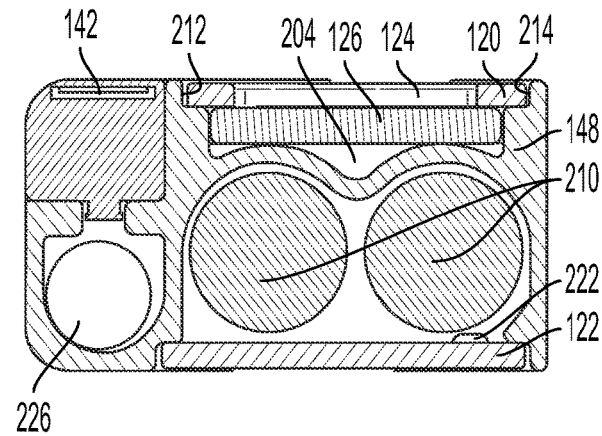
FIG. 6B is a top view of the cross-sectional view of the airflow pathogen reduction system shown in FIG. 4, looking towards the top cap.
Figure 7:
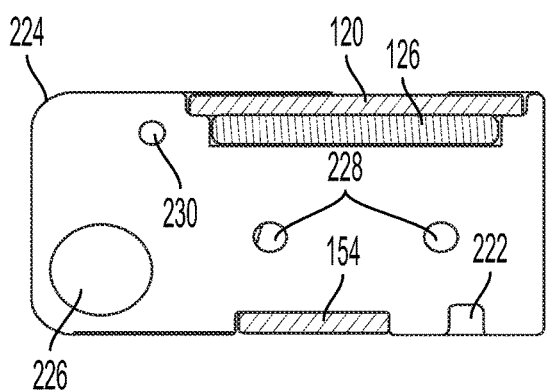
FIG. 7 is a top view of the cross-sectional view of the airflow pathogen reduction system shown in FIG. 4, and including a top plate atop the body.
Figure 8:
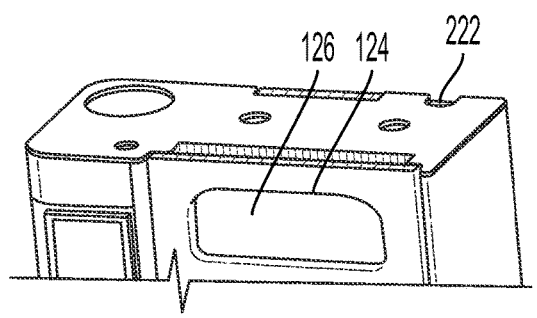
FIG. 8 is a partial perspective view of the cross section of the airflow pathogen reduction system shown in FIG. 7.
Figure 9:
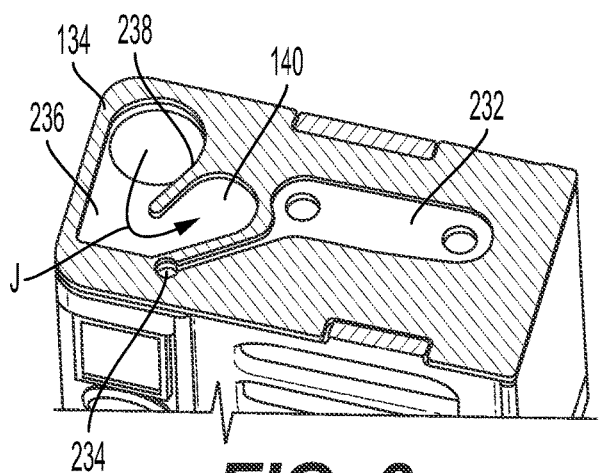
FIG. 9 is a perspective view of a cross section of the airflow pathogen reduction system shown in FIG. 8, and including a bisection of a top cap to revel internal structures of the top cap.
Figure 10:
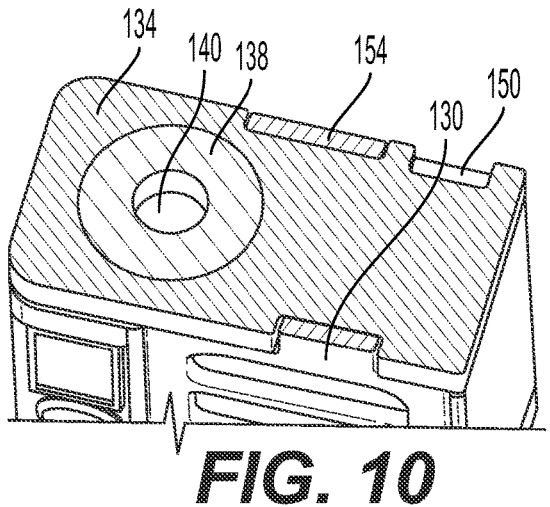
FIG. 10 is a perspective view of a cross section of the airflow pathogen reduction system shown in FIG. 9, showing a non-bisected top cap.
Figure 11:
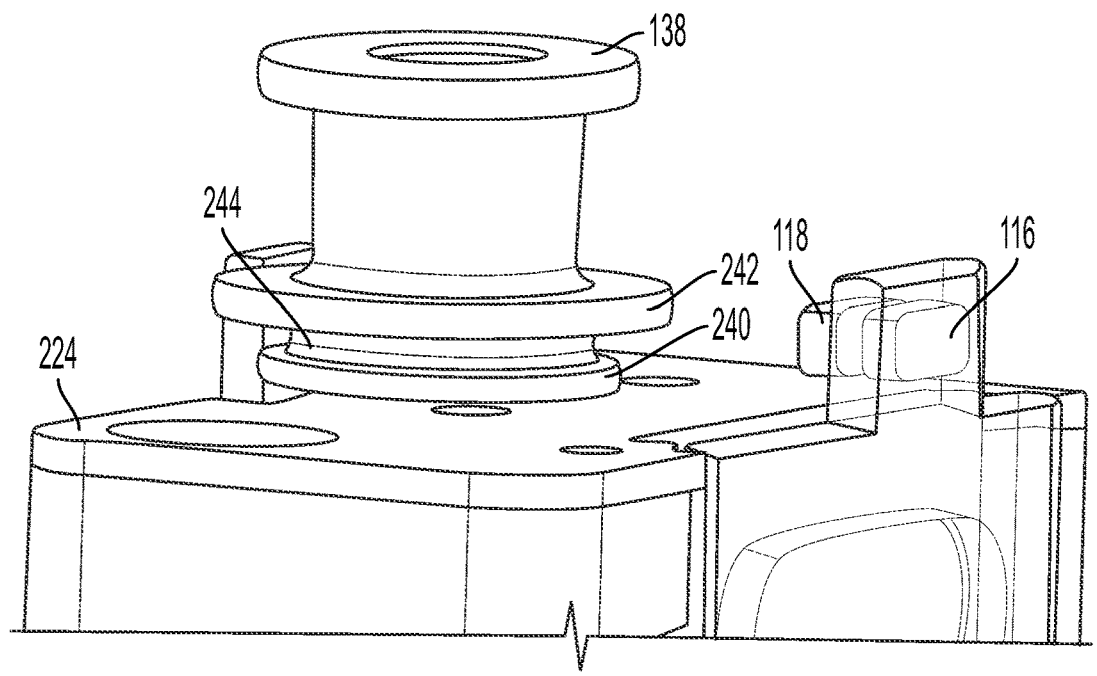
FIG. 11 is a rear side perspective view of a portion of the airflow pathogen reduction system shown in FIGS. 1A-C, pictured with the top cap removed.

FIG. 4 shows another cross-sectional view of the airflow pathogen reduction device 100. Body frame 148 is atop bottom plate 162, and it is shaped such that all cross-sections taken in the vertical axis will be substantially identical. Body 148 generally divides the device 100 into four internal sections: (1) a battery chamber 246 which houses two batteries 210, (2) a section with a filter media 126 and vertical air channels 204,206,208, (3) an illumination chamber 300, and (4) electronics module 202. A cross-section of illumination chamber 300 is provided in FIG. 5. As described, illumination chamber 300 is at least partly formed by body 148. The internal facing walls 310,312,314,316,318 of illumination chamber 300 are highly reflective of UV-C light. In an embodiment, body 148 is made of anodized aluminum, which can provide up to 90% reflection of UV-C wavelength light. In another preferred embodiment, a PTFE material such as POREX® Virtek™ PTFE is used, either for the entire body 148, or for only the illumination chamber 300. POREX® Virtek™ PTFE material can provide up to 97% reflection of UV-C light. In another embodiment, a specialized coating or other UV-C reflective material is used in the composition of at least the illumination chamber 300 walls 310,312,314,316,318.

Illumination chamber 300 has an internal wall 306, which generally forms a tubular shape, wherein a cross-section of the tube resembles the letter "D," having a semicircular end on one half and a rectangular end on the opposite half. The illumination chamber 300 internal wall 306 is comprised of wall sections. The semicircular section of the internal wall 306 includes a vertex 314 on the curved wall portion. The curved section of the internal wall 306 continues on both sides of the curve with wide parallel sections 310,312 which are opposite from and parallel to each other. Wide parallel sections 310,312 are substantially straight sections of the internal walls. The wide parallel sections 310,312 end at an internal corner junction where they meet inwardly extending shoulders 316,318. Inwardly extending shoulders 316,318 are parallel to each other, but perpendicular to wide parallel sections 310,312. Inwardly extending shoulders 316,318 end at an external corner junction where the walls again become parallel to one another, and parallel to wide parallel sections 310,312. These narrow parallel sections 320,322 create a narrow channel extending out from the generally tubular internal wall 306.

A window 302 that is optically transparent to UV-C light is attached to span the space between narrow parallel sections 320,322. In an embodiment, the window is made of fused quartz glass. Behind the window 302 is the electronics module 202 and UV light generator 304. UV light generator 304 is configured to be able to deliver UV-C light through the window 302 into the illumination chamber 300. One possible path that photons emitted from UV light generator 304 can take is shown as path P. The UV-C reflective qualities of the internal wall 306 mean that the UV light generator will emit photons through the window 302, which will travel along a path until the photons reach the internal wall 306. They will reflect off the internal wall 306, and travel in another direction, repeating the sequence of travel and reflect. In one embodiment, the curvature of internal wall 306 is configured to impart multiple reflections within the illumination chamber 300 of any light introduced into the chamber, including at least 25% of the introduced light and in some configurations at least 50% of the introduced light. One advantage of the current device 100 is the optical multiplier of the illumination chamber 300 which maximizes efficiency of emitted UV-C photons, and conserves the photons for maximum reflections before the photons are absorbed into the chamber walls or absorbed by pathogen RNA thereby inactivating pathogens.

In an embodiment, the UV light generator 304 is at least one LED, such as but not limited to a surface mount LED, such as but not limited to XST 3535-UV, manufactured by Luminus in Sunnyvale Calif. In another exemplary embodiment, the UV light generator 304 single or linear array of surface mount LED/s such as but not limited to the 56060-W265-P70-V7.0, manufactured by Bolb Incorporated, Livermore Calif.

Illumination chamber 300 also includes a pressure sensor in pressure communication with the illumination chamber 300. In an embodiment, the pressure sensor is contained within the electronics module 202, with a port 324 into the internal wall 306, giving the sensor access to the pressure environment of the illumination chamber 300. In an embodiment, the pressure sensor port 324 is located in the window 302. Alternate locations for the pressure sensor, and alternate methods for the sensing or measurement of air movement (e.g. from a user's inhale or exhale) are contemplated. The pressure sensor detects any change in pressure within the illumination chamber, thereby detecting for example if a user has inhaled from the device. The pressure sensor communicates this information to the controller and the controller then activates the UV light generator 304. The controller can use a sensed change in pressure, or a threshold amount of a sensed change in pressure as well as a duration of a sensed change in pressure, or any combination to trigger actuation of the UV light generator 304. Use of the pressure sensor to activate the UV light generator 304 ensures that the device 100 conserves power by only activating when actively in use by a user. Additionally, using operator breath to activate the system allows the elimination of a blower, fan or pump. In another embodiment, system activation is controlled by user interface button 144 or external system control via communications interface.

As Exposure is measured in joules of UV-C energy per illumination chamber volume, the present device 100 implements a cross-section of the illumination chamber 300 to have a linear length of high UV-C reflectance. In one configuration, the UV-C LEDs 304 are a linear array situated along the length of the illumination chamber 300 behind the window 302.

The illumination on the inside surface of illumination chamber 300 is highly reflective, uniform and Lambertian. The illumination chamber 300 reflective surface is specular and/or diffuse, the interior optical surface of the present illumination chamber is a >85% UV-C mirror and will cause the LED produced energy to pass through the illumination chamber multiple times with a randomness creating a near uniform photon density within the illumination chamber 300.

As example, if 100 photons leave the UV-C source, such as an LED, in a direction into the illumination chamber 300, then 85 photons will reflect, or bounce, off the anodized aluminum mirror surface of the illumination chamber and travel back through the passing air. These 85 photons will reflect again to 72 then 61, 52, 44, 37, 32, 27. After just 9 reflections the effective number of photon passes is 512. This gain multiplies the photon density calculation by a factor over 5. It is understood that photons absorbed by pathogens (where the photon energy is converted into the destruction of RNA bonds) reduces the number of photons but accomplishes the objective of destruction of the pathogens.

As set forth above, it is contemplated that specialized coatings can improve the reflectance to 97%. Repeating this example with the interior of the illumination chamber 300 either coated or lined with a sleeve of highly UV-C reflective material, the effective multiplier will increase. Using just 9 reflections to compare with the values for anodized aluminum and the same starting 100 photons the 9 reflections have 97, 94, 91, 89, 86, 83, 81, 78, 75 photons, respectively providing an effective multiplier of 8.75. Taking the number of reflections for the light to be reduced to the 27 of the anodized aluminum, with the coated/lined illumination chamber, it then takes 44 reflections to reduce the number of photons to 27, which results in a multiplier of 24.

In another view of this integrating effect, one 100 mW LED creates an 85 mW reflectance illumination source at the mirror surface of the illumination cavity. This in turn creates a 72 mW reflecting source which in turn creates 61 mW, 52 mW, 44 mW, 37 mW, 32 mW, and 27 mW effective sources.

In one configuration of the present device 100, the integrating reflective shape of the illumination chamber 300 is configured such that over the multitude of reflections, the number of photons per $cm^3$ will be fairly uniform and have been effectively multiplied from the emitted number by the number of passes a photon makes before being absorbed by the reflective surface or pathogens. For purposes of illustrative calculations, the multiplying integrating factor is based on just 9 reflections.

The value of photon density, measured in $$\frac{mW}{cm^3}$$

(milli-watts per $cm^3$), the distribution of photons within the illumination chamber 300 and the time a pathogen is present in the illumination chamber 300 determines the probability that enough energy is present to inactivate pathogens to an acceptable viral load that the user's immune system can handle without contracting an infection. This viral load is sometimes referred to as the necessary "dose" of virus to contract an infection.

The photon density (P) is measured in $mW/cm^3$ and best represents the probability a pathogen will be struck. Photon density and the time a pathogen is in the illumination chamber 300 (residence time) defines the Exposure value. The Exposure energy density (E) measured in $mJ/cm^3$ is written:

$$E=Pt$$

As set forth above, the illumination chamber 300 employs the use of reflecting surfaces to "reuse" a photon passing it back through the illumination chamber again. This creates a multiplier effect to the UV-C power generated by the source.

In the *Journal of Quantitative Microbiology* 2, p 249-270, 2000, a *Mathematical Modeling of Ultraviolet Germicidal Irradiation for Air Disinfection* is described by Kowalski et al. as:

$$S=e^{-kIt}$$

Where I is the surface light intensity in $\mu W/cm^2$, t is exposure time and k is a constant that is unique to each pathogen. The value S is the fraction of the of the population that survives.

In the Exposure method:

$$S=e^{-k'E}$$

This gives a direct relationship between the present device 100 and a measure of acceptable pathogen survival. Often the level $D_{37}$ is used, which means that 37% of the pathogens survive and where $E=1/k'$. It should be noted that the constant k may be different than k' since k is determined by survival rate of a pathogen resident on a surface and k' relates to the survival rate of a pathogen existing in an aerosol.

In *Environ. Sci. Technol.* 2007, vol 41, p 5460-5465 *Effect of Ultraviolet Germicidal Irradiation on Viral Aerosols*, Walker and Ko detail that a UV dose of 599 $\mu J/cm^2$ is required for coronavirus population reduction to 12%.

Using just 2 LEDs and an 85% reflectance of the illumination chamber 300, the Exposure drops to 1.2 $mJ/cm^3$ yielding a survival fraction of S=0.39, just slightly higher than the D37 level of 0.37.

To correlate the Exposure method back to the Kowalski equation, the interior surface of the illumination chamber 300 is taken as a surface illumination source. In one configuration, 1.8 watts of effective UV-C light is uniformly distributed on the inside surface area of 31.2 $cm^2$ of the illumination chamber 300. Combining with the time the pathogen is in the illumination chamber, for a 12 LED configuration, the surface power is 2.4 mJ/cm². Adjusting for units, Walker and Ko state a 0.6 mJ/cm² dose gets to 12% survival thus:

$$0.12 = e^{-k*0.6}$$

Solving, provides k=3.53 cm²/mJ
And for one configuration with 12 LEDs:

$$S = e^{-kE} = e^{-(3.53*2.4)} = 2.1 \times 10^{-4} = 0.02\%.$$

Reducing LEDs to 2:

$$S = e^{-kE} = e^{-(3.53*4)} = 0.243 = 24.3\%.$$

To determine the magnitude of the radiation dose, the Exposure is calculated as defined by Exposure=Photon density in units of $$\frac{mW}{cm^3}$$

(milli-watts per cm³) times time in s provides exposure in mJ/cm³.

The time a unit of air is radiated (residence or travel time) is dependent on the path length of the illumination chamber 300 (radiation cavity) and the speed of the air through the illumination chamber 300.

Travel (or residence) Time=path length/velocity

Breath Flow rate Q=Volume/inhale time

Velocity=Flow rate/cross-sectional area of illumination chamber

Reducing the cross section of the illumination chamber 300 to increase intensity is counter intuitive since Exposure may go down due to a greatly increased speed of the air through the illumination chamber.

In one configuration, the illumination chamber 300 has a cross sectional area of 160 mm² and length of 65 mm from inlet to outlet. An often used "standard" for human breathing is a draw of 0.5 liter (500,000 mm³) in 2 seconds which is a flow rate Q of 250,000 mm³/s. Velocity of a pathogen traveling in the airflow is calculated by dividing the flow rate Q by the cross-sectional area relating to a straight through (z axis) pathogen path, and thus the representative flow velocity in the illumination chamber 300 is 1,562.5 mm/s. Velocity divided by the length of the illumination chamber 300 provides the representative exposure time in the chamber of approximately 0.042 seconds.

It is understood that any increase in pathlength within the illumination chamber 300 due to turbulence causing non-z axis velocity would increase the residence time (travel time) in the chamber. Thus, the present straight through calculations illustrate a least or minimum exposure analysis.

In this sample embodiment, Klaran KL265-50 W-SM-WD Engineering sample UV-C LEDs are used in an array of 10 LEDs thermally and electrically bonded to a copper heat sink circuit board. Each LED in the full-on mode produces 80 mW of UV-C light having a 265 nm center wavelength with 4 Watts (W) of electrical input power. This indicates a continuous on heat dissipation requirement of 39.2 Watts for the set of 10 LEDs.

As noted above, the standard breath is a 2 second inhale and is typically associated with a 3 second exhale. LEDs in this embodiment would only be on during the inhale portion of the breathing cycle which relates to "on" duty cycle of 40% (2 seconds of inhalation out of a 5 second cycle). The UV-C LEDS can be driven with a high frequency pulse width modulation, which for purposes of this calculation, is set at a 25% duty cycle. Thus, if the LEDs are powered only during the inhalation cycle (40% of the time) and the LEDs are driven at 25% duty cycle, this provides an overall duty cycle of 10%, which provides the continuous heat dissipation requirement of about 3.92 Watts for the set of 10 LEDs.

For purposes of this example, exposure is calculated only for the 25% duty cycle during the on time since air would be traveling out not in during exhales. Thus, the optical source power would be 0.20 watts of 265 nm UV-light. The reflective optical design of the illumination chamber with highly diffuse reflective surface of 95% in the UV-C region is conservatively estimated to be a "re-use" of these photons relating to 8 times, giving roughly 8 times as many photons as the source photons contributing to the photon density within the illumination chamber. As an example, in one embodiment, POREX © Virtek™ PTFE material is used for the walls of the illumination chamber, with a reflection of 97% in the 265 nm wavelength. This means that 97% of the photons from 265 nm light that hit the surface of the wall will be reflected back out with the same energy and wavelength. This is a "bounce." For the purposes of a conservative estimate, these calculations will solve for a total of 8 bounces before the photons leave the system or are rendered ineffective (i.e. from hitting a pathogen and neutralizing it through absorption, etc.). The amount of time it takes for a given photon to travel from the light source to the reflective wall is dependent on the distance travelled and the speed of light. For clarity and simplicity, we will call the number of photons produced in the amount of time it takes for a photon to travel that distance between the light source and the reflective wall a single photon group. Of each photon group, 97% of those originally-emitted photons will survive the first bounce and will remain effective in the chamber. On the second bounce, 97% of the surviving 97% of the original photon group will remain, which can also be expressed as $(0.97)^2$. Thus there is an exponential relationship between the remaining effective photons and the number of bounces of the photon group. For example, to calculate the proportion of a photon group remaining effective in the system after a given number of bounces, the formula is proportion of reflection raised to the power of the number of bounces. Therefore, to calculate an optical multiplier for a given number of bounces in the system, the sum of these exponentially calculations is made. In other words, after 8 bounces, there are 9 photon groups bouncing around in the system, with one photon group currently emitted by the light (with no reduction in effective photons), a second photon group having bounced one time (with 0.97 photons active), a third photon group having bounced twice (with $0.97^2$ photons active), a fourth photon group having bounced three times (with $0.97^3$ photons active), etc. To calculate the optical multiplier for the system, we would sum together all active photons for each photon group accordingly. The theoretical maximum multiplier as described in calculations for optical integration spheres is:

$$\text{Max Optical Multiplier} = \frac{ref}{(1 - ref)}$$

thus the maximum multiplier for a 95% reflective surface is $$= \frac{.95}{.05} = 19,$$

for an 85% surface is $$= \frac{.85}{.15} = 5.66,$$

and 97% is 33.3. These maximum calculations detail the system performance improvements as a function of reflectance of the illumination cavity surfaces.

As previously described, for the purposes of this calculation we are using a maximum bounce number of 8. Given the optical effectiveness of this system, that estimate is well below the actual total of possible bounces before a photon group is no longer bouncing in the system, and those embodiments of the current system are also contemplated herein. With 8 bounces, there are nine photon groups summed together, as described above, for an optical multiplier of 7.99 times the emitted light energy in W. This means that the total effective light energy remaining in the illumination chamber at any given time after the initial 8 bounces would equal 7.99 times the light energy being emitted from the light at that given time. Using the same method to calculate for eight bounces with 95% effective reflection gives an optical multiplier of 7.40. Using the same method to calculate for eight bounces with 90% effective reflection gives an optical multiplier of 6.13. This describes a system that, in use, can contain over seven times the number of photons available to neutralize pathogens than is being produced by the light source.

We use this optical multiplier to calculate the Exposure of the pathogens to light energy by first calculating photon density in Watts per volume. The effective 265 nm photons in the system after eight bounces is 0.2 W times 7.99 (the optical multiplier described above). This gives a total of 1.6 W of effective light energy, distributed over the total volume of the illumination chamber. In this embodiment, with a cross-sectional area of 160 $mm^2$ and 65 mm length, the volume of the illumination chamber is 10,400 $mm^3$, or 10.4 $cm^3$. Dividing the 1.6 W by the volume gives 0.154 W per $cm^3$, or 154 $mW/cm^3$ of photon density. The photon density is multiplied by the previously calculated time within the chamber of 0.0416 seconds to give an Exposure value of 6.4 $mJ/cm^3$ for the described system.

It has been calculated from the certification testing for an Alpha larger scale prototype that the negative exponential coefficient k' for the challenge pathogen MS2 is −0.375. Using this and the exposure calculated above in our modified Kowalski Survival fraction formula provides a survival fraction of 9% with MS2 pathogens.

$$S=e^{K'E}=e^{(-0.375*6.4)}=0.09=9\%$$

This indicates the embodiment run at these parameters would allow 9% of MS2 pathogens to survive a single pass through the device. It has been stated that the SARS-CoV-2 virus is 10 times easier to inactivate than MS2 so the survival rate for that pathogen would be smaller, perhaps less than 1% survival.

The limitation of the current configurations relates to the ability to dissipate heat due to the inefficiency of current state of the art UV-C LEDs. It is anticipated that as UV-C LEDs become more efficient power UV-C power will increase for a given heat dissipation and survival rates will be further reduced.

FIGS. 6A and 6B show two more cross-sectional views of the airflow pathogen reduction device 100. FIG. 6A shows a cross-section that looks towards the bottom cap 136, while FIG. 6B looks towards the top cap 134. Front door 120 is shown in FIGS. 6A-B, set within body form 148. Body 148 has a first front bezel ridge 212 and a second front bezel ridge 214 which form a bezel to receive front door 120. Likewise, body 148 also has a first rear bezel ridge 216 and a second rear bezel ridge 218 which form a bezel to receive rear door 122.

FIGS. 7 and 8 shows a cross-section of the airflow pathogen reduction device 100. Top plate 224 sits atop body form 148 and electronics module 202. Top exit hole 226 in top plate 224 defines the exit from illumination chamber 300. Top battery holes 228 in top plate 224 provide a retaining means for a battery spring and button connector. Top battery holes 228 also provide a path for wires from the batteries to travel through top plate 224. Top wire hole 230 provides a path for a wire, for example a battery wire, to pass through top plate 224 down into the electronics module 202. Top plate 224 also includes an aperture at the edge for a vent hole 222.

FIG. 9 shows a cross-section of the airflow pathogen reduction device 100. This cross-section bisects the top cap 134 to revel internal structures of top cap 134. There are two main cavities in top cap 134. Top battery connection cavity 232 provides a cavity to receive battery wires from the battery chamber 246, which pass through the top battery holes 228 and the holes in the top battery cavity 232. The battery wires then lay along the cavity 232 and passing through the top wire hole 230 in top plate 224 to go down into the electronics module 202. The second cavity in the top cap 134 is the air exit cavity 236. Air exit cavity 236 has two main lobes separated by an inwardly extending cavity wall 238. Airflow J from the illumination chamber 300 flows upwards through top exit hole 226 and then into air exit cavity 236, in the outer lobe. The airflow then travels around the tip of the inwardly extending cavity wall to the other lobe of air exit cavity 236. This second lobe of air exit cavity 236 is in fluid communication with exit channel 140, allowing the sanitized air from the illumination chamber 300 to be exhausted from the device 100.

FIG. 10 is a cross-sectional view of the airflow pathogen reduction device 100. This view of the top cap shows the embedded strap mount 150. A cross section of embedded mouthpiece 138 in shown in top cap 134. In an embodiment, the embedded mouthpiece 138 is a connector configured to receive tubing. In another embodiment, the embedded mouthpiece 138 is a standalone mouthpiece configured to allow a use to breathe directly out of it.

FIG. 11 is a view of the top portion of airflow pathogen reduction system 100, pictured without top cap 134. This shows the orientation of the embedded magnet 118 in proximity to magnet 116 imbedded in the top tab 130 of front door 120. Embedded magnet 116 is not visible through front door 120, and front door 120 is depicted transparently here only to illustrate the internal placement of embedded magnet 116. Embedded mouthpiece 138 includes a first annular ridge 240 on its bottom edge. Adjacent to first annular ridge 240 is second annular ridge 242. The two annular ridges 240,242 define an annular recess 244 between them. When embedded mouthpiece 138 is installed in top cap 134, the first annular ridge 240 sits below a ring in the top cap 134. The ring sits in the annular recess 244, with annular ridges 240 and 242 providing resistance to movement when installed. Mouthpiece 138 is suitably made from a variety of materials including plastics, polymers, silicone, and other suitable materials known in the art. Additionally, embedded mouthpiece 138 can also function as a tubing connector for use with worn accessories, discussed later. Anytime mouthpiece 138 is described herein, it should be understood that it could interchangeably mean a tubing connector or a mouthpiece. Suitable tubing connectors include compression fit tubing connectors, quick connect tubing connectors, hose barb tubing connectors, pipe thread tubing connectors, John Guest piping connectors, U-bend connectors, and any other suitable means to connect tubing for an airtight gas exchange application, as known in the art.

Figure 12:
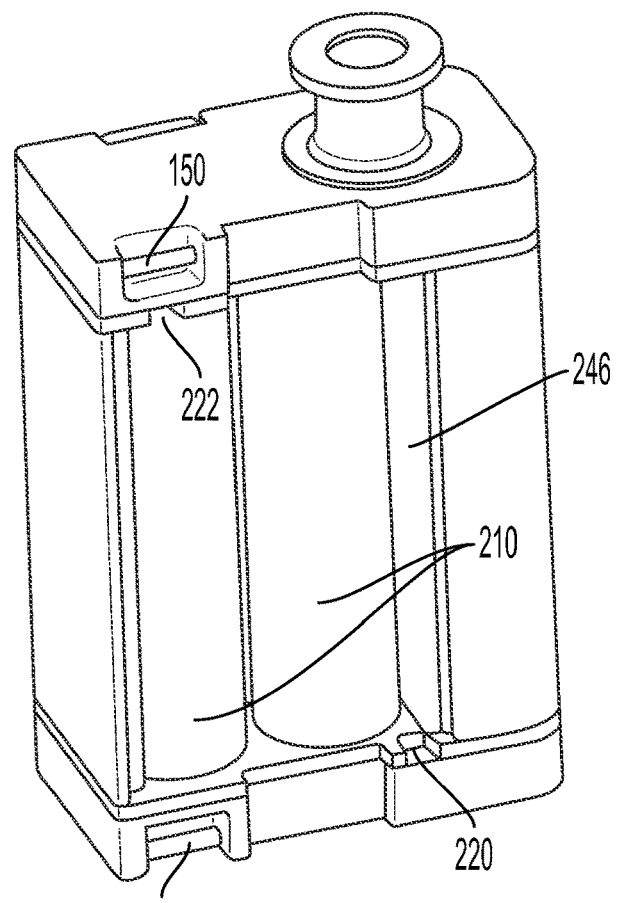
FIG. 12 is a rear perspective view of the airflow pathogen reduction system shown in FIGS. 1A-C, pictured with the rear battery door removed.

FIG. 12 shows a rear view of the airflow pathogen reduction device 100 with the rear door 122 removed. Batteries 210 are shown inside battery chamber 246. In an embodiment the batteries are 18650 batteries (3.7V lithium-ion rechargeable batteries). It is understood that other portable power storage methods known in the art are also appropriate. This includes, but is not limited to, NiCd batteries, NiMH batteries, alkaline batteries, and other means known in the art. FIG. 12 also details the locations of embedded strap mounts 150 in the top 134 and bottom 136 and battery compartment vent slots 220 and 222.

In normal operation of airflow pathogen reduction device 100, a user would inhale through the mouthpiece 138. The inhale through mouthpiece 138 would move the air within the exit channel 140, and illumination chamber 300, thereby presenting a pressure change to the pressure sensor. The pressure sensor communicates with the controller providing a signal that the device 100 is in use, which would trigger the UV light generator 304 to switch on. The illumination chamber 300 would then be actively eliminating pathogens in the airflow. The initiation timing, path length of the illumination chamber 300, the required time for generation of UV light and the pressure sensor sensitivity ae configured to provide sufficient illumination of the passing air in the illumination chamber to provide the desired pathogen inactivation treatment. That is, once inhalation begins, the system must illuminate the passing air before a volume of the air has passed from the device to the user without having be illuminated.

As the user inhales, the negative pressure caused by the air leaving the device 100 will draw more ambient environment air in through the intake apertures 124. The ambient air travels in through intake apertures 124, through filter media 126, and downwards through the vertical air channels 204, 206,208 behind the filter media 126. Once the air reaches the bottom of the vertical air channels 204,206,208, it is now in the bottom cap air channel 160, in the elongate portion of the channel 160. Once in the bottom air cap channel 160, the air travels along flow path F to reach the wider portion of the bottom cap air channel 160, and then upwards through entrance hole 168 in the bottom plate 162. After the air passes through the entrance hole 168, it is in the tubular illumination chamber 300. As the air travels upwards through the illumination chamber 300, the UV-C exposure will inactivate pathogens in the air by the destruction of bonds within the pathogens' RNA. As the treated air moves out of the illumination chamber 300, it passes through exit hole 226 in top plate 224, and then into air exit cavity 234 in top cap 134. The air passes through air exit cavity 234, finally traveling through mouthpiece 138 by way of exit channel 140, before finally exhausting out to the user's inhale.

Additionally, although the components of airflow pathogen reduction device 100 have been described in a unidirectional flow direction, in an embodiment the direction of the airflow is reversed. This embodiment allows a user who is the source of pathogens in the air (i.e. the user has contracted a virus and is actively shedding viral particles in their respiratory droplets and breath) to exhale into the mouthpiece 138, having the exhaled breath trigger the pressure sensor, and treat the exhaled air with UV-C light before the air exhausts out the intake apertures 124. This reverse flow embodiment would protect the surrounding people and ambient environment from exposure to the pathogens in the user's breath. This embodiment is advantageous where a user knows they are contagious, or where a user suspects they may be. It should be noted that reverse flow has been contemplated for all suitable embodiments for which the original airflow is described.

Figure 13A:
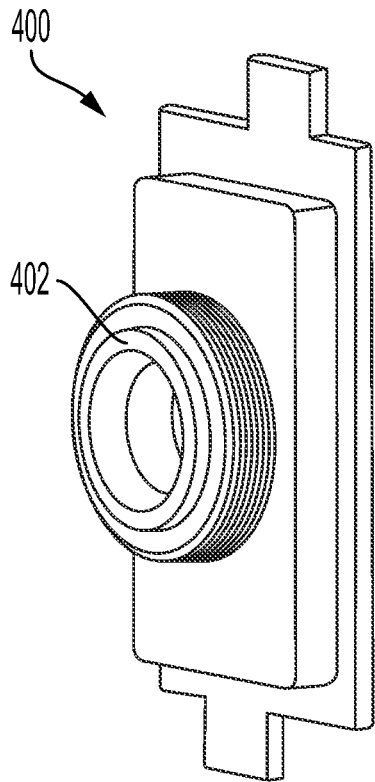
FIG. 13A is a front perspective view of a variation of the front door of the airflow pathogen reduction system, suitable for use in practicing exemplary embodiments of this disclosure.
Figure 13B:
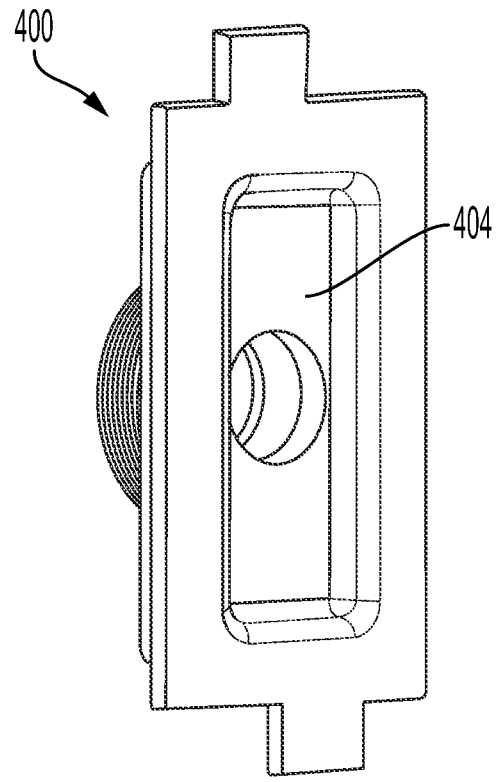
FIG. 13B is a rear perspective view of the front door of the airflow pathogen reduction system shown in FIG. 13A.
Figure 13C:
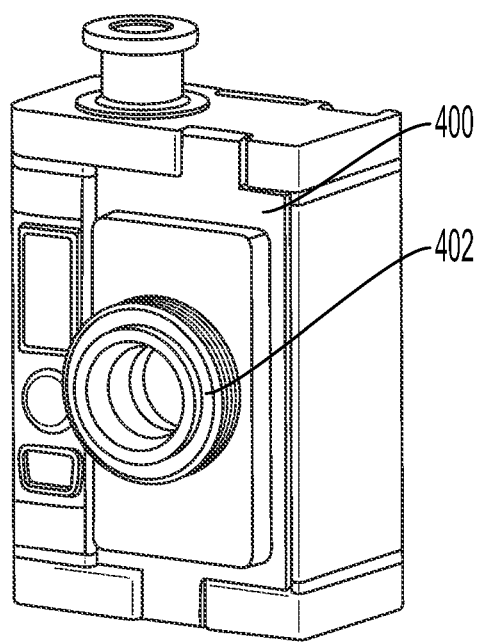
FIG. 13C is a perspective view of the airflow pathogen reduction system with the front door shown in FIGS. 13A and 13B.

FIG. 13A-B show another embodiment of the front door 400. FIG. 13C shows front door 400 in use with airflow pathogen reduction device 100. There is a compression fitting intake 402 in front door 120 which is operable to be coupled to tubing. This embodiment enables a user to use device 100 with a controlled gas intake to be treated, instead of using ambient air for treatment. In an embodiment, a user would attach tubing at one end to compression fitting intake 402, and the other end of tubing to a stream of pretreated air. The stream of pretreated air can be pressurized, thereby generating an assisted draw through device 100. The pressurization in the pressurized air container will "push" the air through the system, requiring less effort on the part of the user. This enables the user to maintain a desired chemical composition in the breathed air, and increases the level of control a user has over the source of the air before UV-C treatment. In addition, an embodiment with pressurized air can assist a user with compromised breathing by lessening the effort required for a user's inhale. Front door 400 also includes a recess 404 on the inside of the front door 400. The recess 404 serves to distribute the incoming airflow over a larger surface area before it contacts filter media 126. Increased filter media 126 surface area exposure makes filter media 126 more effective and more efficient.

Figure 14A:
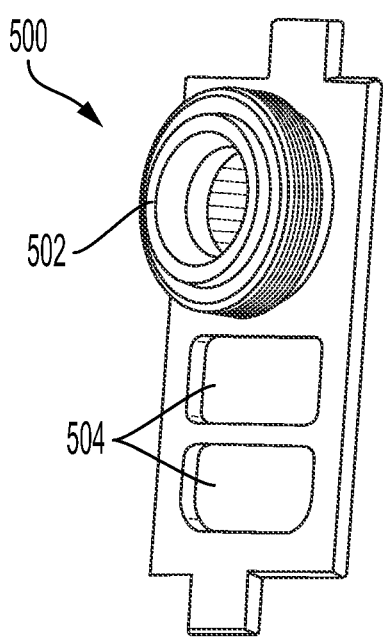
FIG. 14A is a front perspective view of a variation of the front door of the airflow pathogen reduction system, suitable for use in practicing exemplary embodiments of this disclosure.
Figure 14B:
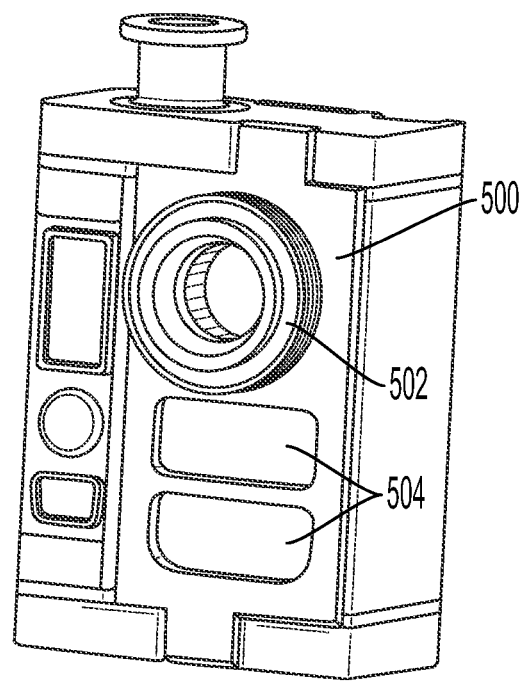
FIG. 14B is a perspective view of the airflow pathogen reduction system with the front door shown in FIGS. 14A and 14B.

FIG. 14A shows an embodiment of front door 500. FIG. 14B shows front door 500 in use with airflow pathogen reduction device 100. Front door 500 includes both a compression fit intake 502, and intake apertures 504. In this embodiment, a user can choose to use a mixture of air supplied by tube and ambient air from the environment. Regardless of whether the air comes in through the intake apertures or through the compression fit intake, it then passes through filter media 126 and continues through to the vertical air channels 204,206,208. Front door 500 can also accommodate use with pressurized air, as described above, which allows control over air composition as well as an opportunity for pressure-assisted breathing. In addition, front door 500 can accommodate the use of pressurized oxygen from a canister that will mix with ambient air from the intake apertures 504.

Figure 15:
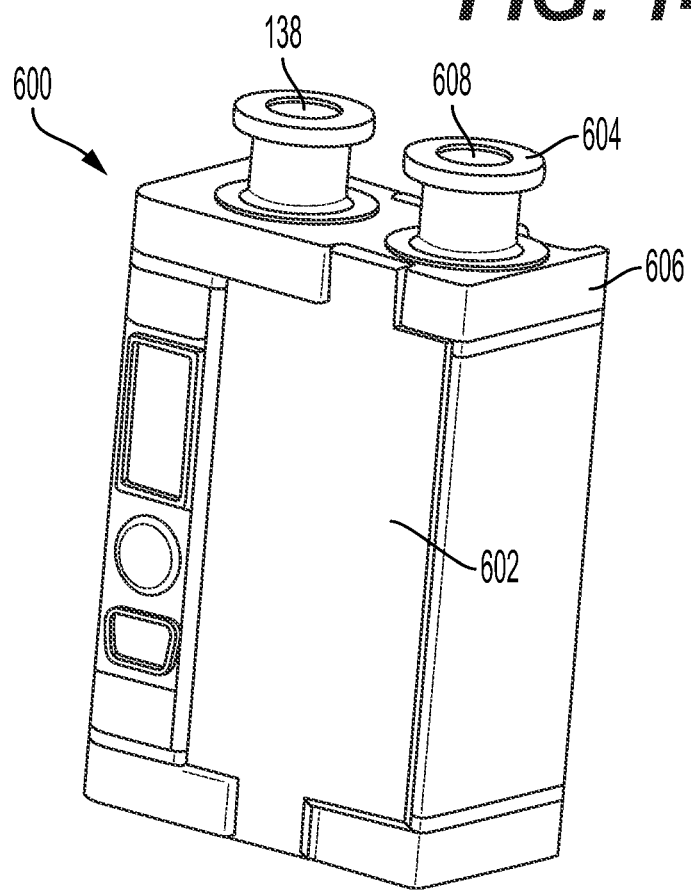
FIG. 15 is a perspective view of the airflow pathogen reduction system with a variation of the front door.

FIG. 15 is an embodiment of front door 602 in use with an embodiment of airflow pathogen reduction device 600. Front door 602 is a solid door with no intake channel. The front door 602 is sealed to the body so as not to allow ambient air to penetrate the system. Intake tubing connector 604 is embedded in top cap 606, which has apertures to support two embedded connectors 138,604. In this embodiment there is no filtration of the airflow. The air enters device 600 through intake channel 608 in intake tubing connector 604. The airflow then proceeds through the at least one vertical air channel 204. The advantage to this configuration is the minimization of bulkiness on the device with the flush front door 602 and the elimination of the bulk of having a tube connected laterally to an intake means on the front door 602. Instead, the tubing and connectors are all at the top of the device 600, accommodating scenarios where a smaller device is more convenient such as containing the device in a pocket.

FIG. 16 shows an embodiment of front door 700 in use with airflow pathogen reduction device 100. Front door 700 includes an intake tubing connector 704 with an intake channel 706. Front door 700 also includes a protrusion that accommodates room for filter media 126 behind the front door 700. The filter media can be removed or included during use, depending on the user's needs. It should be understood that while many of the presently disclosed embodiments include filter media 126, the present disclosure also contemplates that a filter media 126 may not be used. One advantage of using front door 700 is that when the reverse flow mode is used with this configuration, the exhaled breath passes through filter media 126 before it enters the device 100. This prevents some particulate matter in the breath from entering the device, thereby keeping the interior of the device cleaner for longer. In this reverse flow mode, the user exhales through a tube (i.e. with a wearable accessory) connected to intake tubing connector 704, and the exhaled breath enters the device through intake channel 706. The exhaled breath then travels through filter media 126, held behind front door 700. From there, the exhaled breath takes the same path as described before, through the vertical air channels, through the illumination chamber, etc., except that the treated air is vented to the ambient environment, not routed to a user.

FIG. 17 shows an embodiment of front door 800 in use with airflow pathogen reduction device 100. Front door 800 includes intake apertures 804 as well as a quick connect tubing connector 802. This system allows for a mix of controlled oxygen with ambient air to be taken in together.

Figure 18:
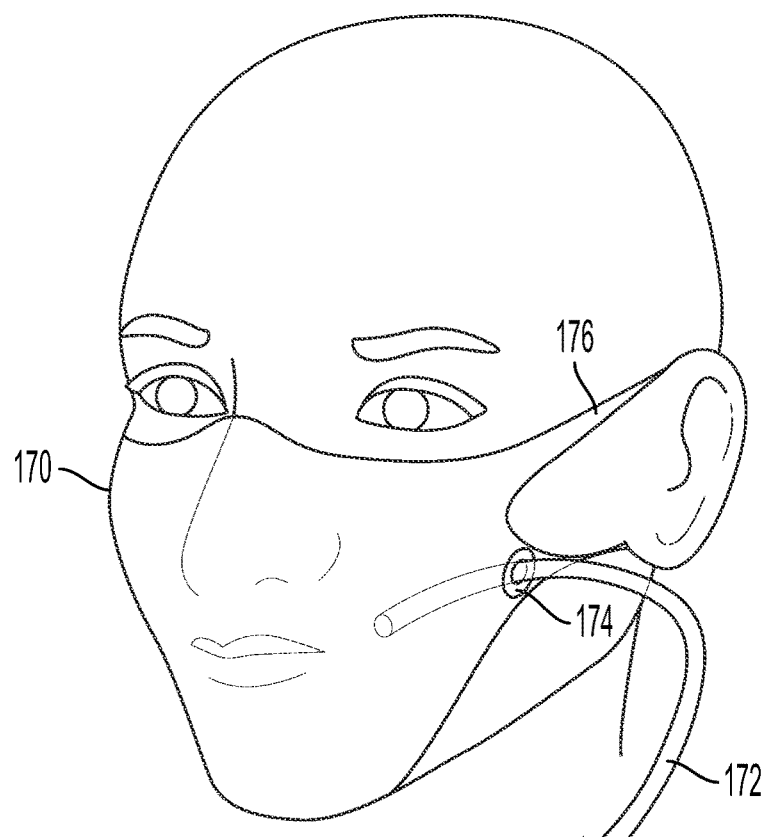
FIG. 18 is a perspective view of an exemplary embodiment of the user-end connector of the airflow pathogen reduction system in use by a user.

FIG. 18 shows a user wearing silicone mask 170 as a user-end wearable accessory. Tubing 172 is connected at one end to airflow pathogen reduction device 100, to receive treated air. Tubing 172 is connected at the opposite end to sealed tube coupling 174, where tubing 172 vents the airflow from the device 100 to the interior of the silicone mask 170. The silicone mask 170 itself should be fitted to the user's face, either through custom fitting or through molded options for consumers. There should be an airtight seal between the user's face and the silicone mask 170, such that the ambient air of the environment will not penetrate the interior of the mask 170. Ear straps 176 or other means to fasten the mask onto a user's head will help ensure that the mask remains sealed to the user's face. The mask 170 covers the nose and mouth of the user. If the interior of the mask 170 remains sealed off from the ambient environment, then the user can inhale only treated air supplied by device 100. In an embodiment there is provided a check valve so that when a user exhales, the air is diverted and exhausted out a separate tube end, not the end connected to the device 100. The check valve can be anywhere in the tubing 172, or in a separate tube which is also in airtight fluid communication with the interior of the silicone mask 170.

Figure 19:
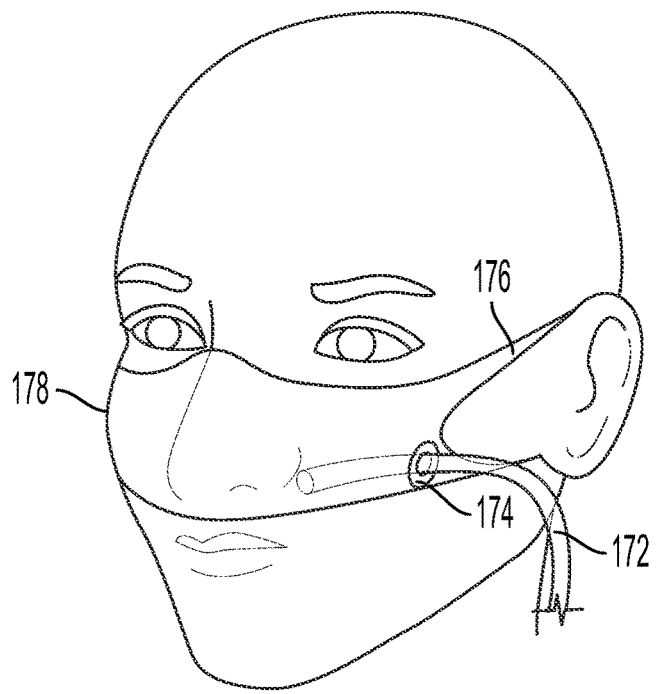
FIG. 19 is a perspective view of an exemplary embodiment of the user-end connector of the airflow pathogen reduction system in use by a user.

FIG. 19 shows a user wearing a silicone nose mask 178 as a user-end wearable accessory. In this embodiment, the silicone mask 178 is configured to cover only the nose of a user, leaving the mouth open to the ambient environment. Tubing 172 vents the treated airflow from the device 100 to the interior of the silicone mask 178. This enables a user to intake breaths through the nose, of treated air, and exhale breaths through the mouth. It also enables a user to use the device 100 while engaging in an activity where the mouth is needed, like eating a meal. If a user wears nose mask 178 while eating, the user can intake breaths through the nose of treated air, and use their mouth normally while eating and talking. In an embodiment there is provided a check valve so that when a user exhales, the air is diverted and exhausted out a separate tube end. The check valve can be anywhere in the tubing 172, or in a separate tube which is also in airtight fluid communication with the interior of the silicone mask 178. In this configuration, a user could inhale treated air through the nose, and exhale either by mouth or by nose, through the check valve.

Figure 20:
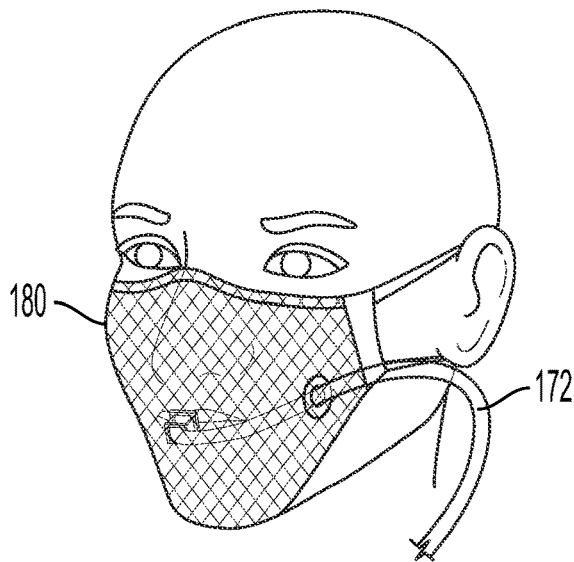
FIG. 20 is a perspective view of an exemplary embodiment of the user-end connector of the airflow pathogen reduction system in use by a user.
Figure 21:
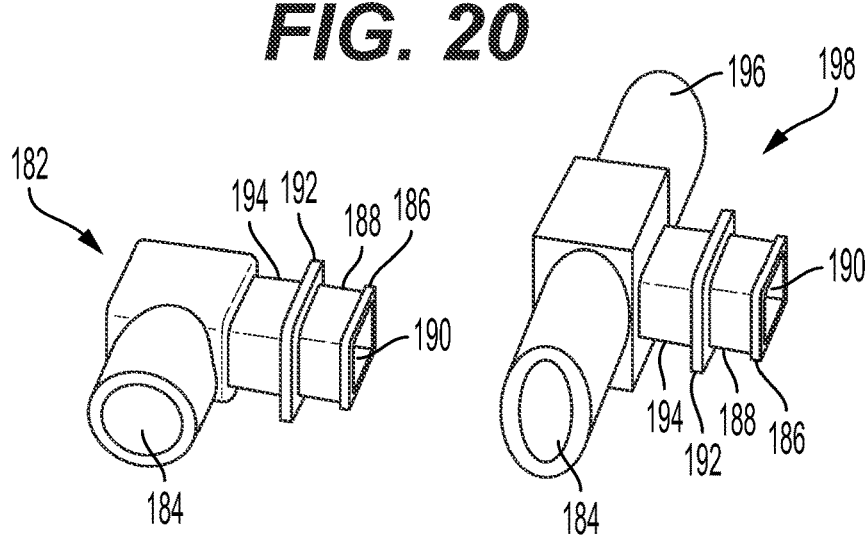
FIG. 21 is a top perspective view of two interchangeable mouthpieces suitable for use with the airflow pathogen reduction system.
Figure 22:
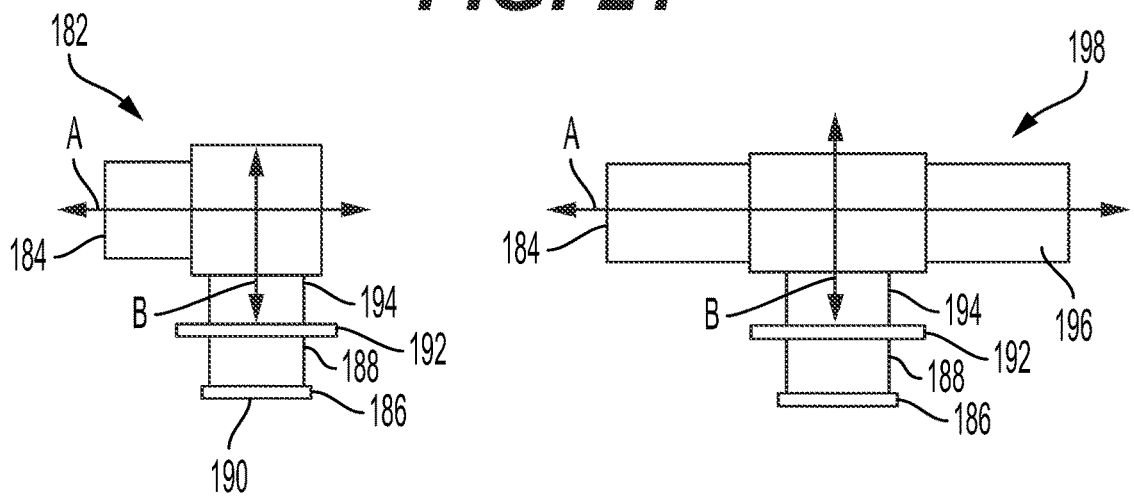
FIG. 22 is a top view of the interchangeable mouthpieces shown in FIG. 21.

FIG. 20 shows a user wearing a cloth mask 180 over a mouthpiece user-end accessory. FIGS. 21 and 22 show two alternative embodiments of a mouthpiece 182,198. Mouthpiece 182 includes a cylindrical mouthpiece intake 184, which is oriented along the length of an axis A. It also includes a cuboid airflow channel 190 which is oriented along the length of an axis B. In an embodiment axes A and B are perpendicular to one another, forming an airflow path shaped like an "L," and joining intake 184 with airflow channel 190 at a corner. The airflow channel includes an outer ridge 186, a bite tube 188, a lip seal ridge 192, and a lip relief tube 194. When a user places the mouthpiece 182 in their mouth, the outer ridge 186 should sit behind the teeth, the teeth themselves resting on and around the bite tube 188. The user's lips should sit on the lip relief tube 194, and the lip seal ridge 192 should sit behind the lips but in front of the teeth, creating a seal where the ridge comfortably overlaps the inside of the user's lips. Tubing 172 can be connected at one end to device 100 and at the other end to intake 184. This configuration would allow a user to inhale through the mouthpiece, thereby taking in treated air but exhale through the nose. A user could use the mouthpiece embodiment with or without a cloth mask on top of it.

Mouthpiece 198 is substantially similar to mouthpiece 182, but it includes an elliptic cylinder-shaped mouthpiece intake 184 and mouthpiece exit 196. The intake 184, exit 196, and airflow channel 190 are joined to look like a "T," wherein the intake 184 and exit 196 are oriented successively along axis A, and airflow channel 190 joins them at the center point, oriented along axis B, where axis B is perpendicular to axis A. A user would use mouthpiece 198 in a similar way to mouthpiece 182, but mouthpiece 198 has a separate exit for exhausting exhaled breath. There is provided a check valve somewhere in the airflow system that will divert exhaled breath out through exit 196, and will intake treated air through intake 184.

FIG. 23 shows a nose draw system 900, for use with airflow pathogen reduction device 100 as a user-end wearable accessory. Nose draw system 900 is generally shaped like a hollow semi ellipsoid, with the mask portion of the system 900 forming a cup with a top edge 902 and a bottom edge 904. The cup is configured to cover the nose of a user, where the top edge 902 rests on the bridge of a user's nose, and the bottom edge 904 rests between the user's nostrils and upper tooth line (on the upper philtrum). The cup should create an airtight seal with the user's skin, to reduce leakage. The cup includes two apertures 906,908 in the interior of the cup, each leading to a tubing connector 910,912. The first aperture 906 leads to the first tubing connector 910, while the second aperture 908 leads to the second tubing connector 912. The first tubing connector is connected to intake tubing 918, which carries treated air from device 100 to the mask system 900. The second tubing connector is connected to a check valve 914 for exhausting the exhaled breath and exhaust tubing 916. There is also included a strap 920 for fastening the nose draw system 900 around a user's head. This strap 920 also, in an embodiment, includes a guide shaft to encase tubing, to hold the tubing away from the rest of the user's face. This system 900 is advantageous in situations where treated air is desired, but where it is more convenient to use the mouth normally, e.g. eating or talking.

The invention claimed is:

1. A handheld apparatus for presenting treated air to a user, the apparatus comprising:
   (a) a handheld housing having an inlet and an outlet;
   (b) a power source retained in the handheld housing;
   (c) a controller in the handheld housing and operably connected to the power source;
   (d) a flow path extending through the handheld housing from the inlet to the outlet;
   (e) a UV generator in the handheld housing, the UV generator optically coupled to the flow path; and
   (f) a mouthpiece without a mask for covering a mouth and nose of the user, the mouthpiece embedded at the outlet and integral with the handheld housing without tubing, the mouthpiece having a mouthpiece body configured for positioning directly in the mouth of the user to sealingly engage the mouth with the mouthpiece.

2. The apparatus of claim 1, wherein the mouthpiece further comprises a lip seal ridge coupled to the mouthpiece body and configured to be positioned behind a set of lips of the user to sealingly engage the set of lips of the user to the lip seal ridge.

3. The apparatus of claim 1, wherein the mouthpiece includes a check valve.

4. The apparatus of claim 1, wherein the mouthpiece further comprises an outer ridge spaced from the lip seal ridge, the outer ridge coupled to the mouthpiece body and configured to be positioned behind a set of teeth of the user, and wherein the mouthpiece body is a bite tube configured for the set of teeth of the user to rest thereon.

5. The apparatus of claim 1, wherein the UV generator is one or more LEDs.

6. The apparatus of claim 1, wherein the controller is configured to activate the UV generator in response to user input.

7. The apparatus of claim 6, wherein the user input is one of an imparted pressure change in the flow path, actuation of a switch, an imparted pressure change in the flow path and actuation of a switch, and an external control signal.

8. The apparatus of claim 1, further comprising an intake air filter cavity fluidly connected to the flow path.

9. The apparatus of claim 1, wherein the flow path includes an illumination chamber, the illumination chamber having a combination of diffuse and specular UV-C reflecting surface of at least 85% mirror.

10. The apparatus of claim 9, wherein energy produced by the UV generator passes through the illumination chamber multiple times to provide a gain wherein the photon density is multiplied by at least 5.

11. A handheld apparatus for presenting treated air to a user, the apparatus comprising:
    (a) a handheld apparatus body having at least one inlet and at least one outlet;
    (b) a power source;
    (c) a flow path through the handheld apparatus body from the at least one inlet to the at least one outlet;
    (d) an illumination chamber in the flow path, the illumination chamber comprising: a plurality of UV light sources uniformly spaced along a length of the illumination chamber and in electrical connection with the power source and operable to emit photons over time; and
    UV reflective walls, wherein at least a portion of the photons emitted by the plurality of UV light sources are reflected by the UV reflective walls at least five times; and
    (e) a mouthpiece without a mask for covering a mouth and nose of the user, the mouthpiece embedded at the at least one outlet and integral with the handheld housing without tubing, the mouthpiece having a mouthpiece body configured for positioning directly in the mouth of the user to sealingly engage the mouth with the mouthpiece.

12. The apparatus of claim 11, wherein the UV-reflective walls have a UV reflection effectiveness of at least 90%.

13. A method of presenting treated air to a user, the method comprising:
    (a) sealingly engaging a mouth around a body of a mouthpiece embedded at an outlet and integral to a body of a handheld housing; and
    (b) generating air movement through an illumination chamber having a flow channel in the handheld housing by an inhalation of the user to impart an initiation signal to a controller retained in a handheld housing and to expose the moved air to a plurality of UV light sources uniformly spaced along the length of the illumination chamber, wherein energy produced by the plurality of UV light sources passes through the illumination chamber multiple times to provide a gain wherein the photon density is multiplied by at least 5; and
    wherein the mouthpiece does not have a mask for covering a mouth and nose of the user, the mouthpiece embedded at the at least one outlet and integral with the handheld housing without tubing, the mouthpiece having a mouthpiece body configured for positioning directly in the mouth of the user to sealingly engage the mouth with the mouthpiece.

14. The method of claim 13 wherein the moving of the air is effected by a user's exhalation.

15. The method of claim 13, wherein the moving of the air is effected by a user's inhalation.

16. The method of claim 13, further comprising optically isolating the mouthpiece from the emitted UV radiation.

17. A method of presenting treated air to a user, the method comprising:
    (a) providing a first duty cycle comprising
        (i) cycling on a plurality of UV light sources uniformly spaced along the length of an illumination chamber in an airflow channel in a handheld housing, during inhalation of a user to emit photons into an air flow in the illumination chamber in the airflow channel, wherein at least a portion of the emitted photons are reflected within the illumination chamber at least 3 times and
        (ii) cycling the plurality of UV light sources off during an exhalation of a user to terminate emitting photons corresponding to at least one of a flow through the airflow channel and a pressure in the airflow channel;
    (b) providing a second duty cycle comprising driving the plurality of UV light sources with a high frequency cycle when the plurality of UV light sources is cycled on according to the first duty cycle, wherein the overall duty cycle of the first duty cycle multiplied by the second duty cycle is less than 25%, wherein a heat dissipation requirement of the plurality of UV light sources is less than 40 W; and
    sealingly engaging a mouth around a body of a mouthpiece embedded at an outlet and integral to a body of the handheld housing; and
    wherein the mouthpiece does not have a mask for covering a mouth and nose of the user, the mouthpiece embedded at the at least one outlet and integral with the handheld housing without tubing, the mouthpiece having a mouthpiece body configured for positioning directly in the mouth of the user to sealingly engage the mouth with the mouthpiece.

18. The method of claim 13, further comprising the steps of:
(c) providing a first duty cycle comprising (i) cycling the plurality of UV light sources on during inhalation of a user to emit photons into an air flow in an illumination chamber in an airflow channel, wherein at least a portion of the emitted photons are reflected within the illumination chamber at least 3 times and (ii) cycling the plurality of UV light sources off during an exhalation of a user to terminate emitting photons corresponding to at least one of a flow through the airflow channel and a pressure in the airflow channel;
(d) providing a second duty cycle comprising driving the plurality of UV light sources with a high frequency cycle when the plurality of UV light sources is cycled on according to the first duty cycle, wherein the overall duty cycle of the first duty cycle multiplied by the second duty cycle is less than 25%, and wherein the heat dissipation requirement is less than 40 W.

19. The apparatus of claim 11, wherein the mouthpiece further comprises a lip seal ridge coupled to the mouthpiece body and configured to be positioned behind a set of lips of the user to sealingly engage the set of lips of the user to the lip seal ridge.

20. The apparatus of claim 19, wherein the mouthpiece further comprises an outer ridge spaced from the lip seal ridge, the outer ridge coupled to the mouthpiece body and configured to be positioned behind a set of teeth of the user, and wherein the mouthpiece body is a bite tube configured for the set of teeth of the user to rest thereon.

21. The apparatus of claim 11, wherein the handheld apparatus body includes a first end cap at one end of the illumination chamber and a second end cap at a second end of the illumination chamber, the first and second end caps each having a UV-C reflective surface coating, wherein the first and second end caps are configured to reflect UV-C light from the UV light source back into the illumination chamber to increase the number of bounces of photons off the UV reflective walls.

22. The apparatus of claim 1, wherein the UV generator is a plurality of UV light sources driven with a high frequency pulse width modulation having a heat dissipation requirement of less than 40 Watts.

23. The apparatus of claim 1, wherein the UV generator is a plurality of UV light sources driven with a high frequency pulse width modulation having a heat dissipation requirement of less than 4 Watts.

24. The method of claim 13, wherein the plurality of UV light sources has a heat dissipation requirement of less than 4 Watts.

25. The method of claim 17 wherein the plurality of UV light sources has a heat dissipation requirement of less than 4 Watts.

26. The method of claim 17 wherein energy produced by the plurality of UV light sources is reflected within the illumination chamber to provide a gain wherein the photon density is multiplied by at least 5.

* * * * *